(12) United States Patent
Wang et al.

(10) Patent No.: US 11,896,849 B2
(45) Date of Patent: Feb. 13, 2024

(54) SUBJECT POSITIONING SYSTEMS AND METHODS

(71) Applicant: SHANGHAI UNITED IMAGING HEALTHCARE CO., LTD., Shanghai (CN)

(72) Inventors: Yifeng Wang, Shanghai (CN); Yige Zhang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 13 days.

(21) Appl. No.: 17/649,366

(22) Filed: Jan. 30, 2022

(65) Prior Publication Data

US 2022/0152423 A1    May 19, 2022

Related U.S. Application Data

(63) Continuation of application No. 16/729,402, filed on Dec. 29, 2019, now Pat. No. 11,235,176.

(30) Foreign Application Priority Data

Dec. 29, 2018  (CN) ......................... 201811642275.X

(51) Int. Cl.
*A61N 5/10* (2006.01)
*G06T 7/246* (2017.01)
(Continued)

(52) U.S. Cl.
CPC ............. *A61N 5/1049* (2013.01); *G03H 1/02* (2013.01); *G06T 7/0012* (2013.01); *G06T 7/246* (2017.01);
(Continued)

(58) Field of Classification Search
CPC .......... A61N 5/1049; A61N 2005/1051; A61N 2005/1055; A61N 2005/1062;
(Continued)

(56) References Cited

U.S. PATENT DOCUMENTS 4,296,329 A    10/1981   Mirabella
7,453,984 B2*  11/2008   Chen .................... A61N 5/1049
                                                      378/92
(Continued)

FOREIGN PATENT DOCUMENTS

CN    201734722 U    2/2011
CN    101869870 B    9/2013
(Continued)

OTHER PUBLICATIONS

Dong, Feng et al., Measurement Method of Medical Robot Positioning System Based on Binocular Vision, Journal of Optoelectronics Laser, 25(5): 1027-1034, 2014.
(Continued)

*Primary Examiner* — Marcus H Taningco
(74) *Attorney, Agent, or Firm* — METIS IP LLC

(57) ABSTRACT

Subject positioning systems and methods are provided. A method may include obtaining first information of at least part of a subject when the subject is located at a preset position, and determining, based on the first information, a first position of each of one or more feature points located on the at least part of the subject. The method may include obtaining, using an imaging device, second information of the at least part of the subject when the subject is located at a candidate position. The method may further include determining, based on the second information, a second position of each of the one or more feature points, a first distance between the first position and the second position for each feature point of the one or more feature points, and a target
(Continued)

position of the subject based at least in part on the one or more first distances.

20 Claims, 9 Drawing Sheets

(51) Int. Cl.
*G03H 1/02* (2006.01)
*G06T 7/00* (2017.01)

(52) U.S. Cl.
CPC ............... *A61N 2005/1051* (2013.01); *A61N 2005/1055* (2013.01); *A61N 2005/1062* (2013.01); *G06T 2207/30004* (2013.01)

(58) Field of Classification Search
CPC ............ A61N 5/1037; A61N 2005/105; A61N 2005/1056; A61N 2005/1061; A61N 5/107; A61N 2005/1059; A61N 2005/1063; A61N 2005/1076; A61N 5/1067; A61N 2005/1054; G03H 1/02; G03H 1/2249; G03H 5/00; G03H 2210/30; G06T 7/0012; G06T 7/246; G06T 2207/30004; G01V 8/005; A61B 6/08

See application file for complete search history.

(56) References Cited

U.S. PATENT DOCUMENTS

| | | | |
|---|---|---|---|
| 11,235,176 B2* | 2/2022 | Wang | G03H 1/2249 |
| 2002/0085668 A1* | 7/2002 | Blumhofer | A61N 5/1049 |
| | | | 378/68 |
| 2005/0096515 A1* | 5/2005 | Geng | A61N 5/1049 |
| | | | 600/315 |
| 2008/0101669 A1 | 5/2008 | Jeung | |
| 2009/0052760 A1 | 2/2009 | Smith et al. | |
| 2015/0352376 A1 | 12/2015 | Wiggers et al. | |
| 2016/0129283 A1 | 5/2016 | Meir et al. | |
| 2017/0186157 A1 | 6/2017 | Boettger et al. | |
| 2017/0310953 A1 | 10/2017 | Hanson et al. | |
| 2017/0360402 A1 | 12/2017 | De Jonge et al. | |
| 2018/0099154 A1 | 4/2018 | Prieels | |
| 2018/0339174 A1 | 11/2018 | Kilby et al. | |
| 2019/0054322 A1* | 2/2019 | Yang | A61N 5/1081 |
| 2019/0308033 A1 | 10/2019 | Nishio et al. | |
| 2020/0138329 A1 | 5/2020 | Reilly et al. | |

FOREIGN PATENT DOCUMENTS

| | | |
|---|---|---|
| CN | 106621078 A | 5/2017 |
| CN | 106943678 A | 7/2017 |
| CN | 106949835 A | 7/2017 |
| CN | 107510467 A | 12/2017 |
| CN | 108619621 A | 10/2018 |
| CN | 108853755 A | 11/2018 |
| WO | 2013059358 A2 | 4/2013 |
| WO | 2017145155 A1 | 8/2017 |

OTHER PUBLICATIONS

First Office Action in Chinese Application No. 201811642275.X dated Apr. 15, 2020, 27 pages.

Notification to Grant Patent Right for Invention in Chinese Application No. 201811642275.X dated Jun. 24, 2021, 8 pages.

* cited by examiner

300

SUBJECT POSITIONING SYSTEMS AND METHODS

CROSS-REFERENCE TO RELATED APPLICATIONS

This application is a continuation of U.S. application Ser. No. 16/729,402, filed on Dec. 29, 2019, which claims priority to Chinese Patent Application No. 201811642275 X, filed on Dec. 29, 2018, the contents of each of which are hereby incorporated by reference.

TECHNICAL FIELD

The present disclosure generally relates to systems and methods for positioning a subject, and in particular, to systems and methods for determining a position of a subject based on a holographic projection device.

BACKGROUND

Radiotherapy is widely used in treatment for cancer and other conditions. Conventionally, in radiotherapy localization, a position of a subject with a region to be irradiated by radiation beam may be determined by using a radiotherapy positioning device (e.g., a radiotherapy simulator), and one or more markers (e.g., a cross) may be labeled on the surface of the subject to assist in recording the position of the subject. At this position, the region coincides with the isocenter of a radiotherapy device. During the radiotherapy treatment, the markers and laser lamps may be used to positioning the subject to ensure the region coincides with the isocenter again. However, a change (e.g., a loss of one or more markers, a position change of one or more markers caused by a morphological change of the subject, etc.) may lead to a misalignment between the region of the subject and the isocenter of the radiotherapy device. Thus, it may be desirable to develop effective systems and methods for positioning a subject in a medical device.

SUMMARY

According to an aspect of the present disclosure, a method for positioning a subject is provided. The method may be implemented on a computing device having one or more processors and one or more storage devices. The method may include obtaining first information of at least part of a subject when the subject is located at a preset position. The first information may include at least a first set of position data of the at least part of the subject. The method may include determining, based on the first information, a first position of each of one or more feature points located on the at least part of the subject. The method may include obtaining, using an imaging device, second information of the at least part of the subject when the subject is located at a candidate position. The second information may include at least a second set of position data of the at least part of the subject. The method may further include determining, based on the second information, a second position of each of the one or more feature points. The method may further include determining, based on the second information, a second position of each of the one or more feature points for each feature point of the one or more feature points. The method may further include determining, based at least in part on the one or more first distances, a target position of the subject.

In some embodiments, the imaging device includes a holographic projection device. Obtaining second information of the at least part of the subject using the imaging device may include obtaining first scanning data by causing the holographic projection device to image the subject using a millimeter wave, and obtaining the second information based on the first scanning data.

In some embodiments, the one or more feature points may include at least a marker located on a surface of the subject, the marker indicating a region of interest (ROI) of the subject.

In some embodiments, determining, based at least in part on the one or more first distances, a target position of the subject may include determining the target position of the subject based on a determination result of whether the first distance is less than a first threshold.

In some embodiments, the determination result may include that the first distance is less than the first threshold. Determining the target position of the subject based on a determination result of whether the distance is less than a first threshold may include designating the candidate position as the target position of the subject.

In some embodiments, the determination result may include that the first distance exceeds the first threshold. Determining the target position of the subject based on a determination result of whether the distance is less than a first threshold may include adjusting the candidate position of the subject to an adjusted position such that, for each of the one or more feature points, a second distance between a third position of the feature point and the first position of the feature point is less than the first threshold, wherein the third position is obtained based on third information of the at least part of the subject, and the third information includes at least a third set of position data of the at least part of the subject. Determining the target position of the subject based on a determination result of whether the distance is less than a first threshold may further include designating the adjusted position as the target position of the subject.

In some embodiments, the method may further include obtaining fourth information of the at least part of the subject using the imaging device at a time interval during a radiation session. The fourth information may include at least a fourth set of position data of the at least part of the subject. The method may further include determining, based on the fourth information, a fourth position of each of the one or more feature points. The method may further include causing, based on a third distance between the fourth position and the first position of each of the one or more feature points, a radiation assembly to perform a preset operation corresponding to the third distance.

In some embodiments, causing, based on a third distance between the fourth position and the first position of each of the one or more feature points, a radiation assembly to perform a preset operation corresponding to the third distance may include controlling an operation of the radiation assembly based on a second determination result of whether the third distance is less than the first threshold.

In some embodiments, the second determination result may include that the third distance exceeds the first threshold. Controlling an operation of the radiation assembly based on a second determination result of whether the third distance is less than the first threshold may include causing the radiation assembly to stop emitting radiation beams.

In some embodiments, the method may further include obtaining second scanning data by scanning a target area with the imaging device, wherein the target area includes the subject and a motion area of a radiation assembly. The method may further include obtaining fifth information of the target area based on the second scanning data. The fifth information may include at least a fifth set of position data of the target area. The method may further include obtaining a motion trajectory of the radiation assembly. The method may further include predicting, based on the fifth information and the motion trajectory, whether the subject and the radiation assembly are going to collide. The method may further include adjusting a position of the subject based on a prediction result of whether the subject and the radiation assembly are going to collide.

According to another aspect of the present disclosure, a method for positioning a subject is provided. The method may be implemented on a computing device having one or more processors and one or more storage devices. The method may include obtaining, using an imaging device, target information of at least part of a subject when the subject is located at a preset position. The target information may include at least a set of target position data of the at least part of the subject. The method may include generating, based on the target information, a virtual representation of the at least part of the subject. The method may include comparing the virtual representation of the at least part of the subject and the at least part of the subject located at each of one or more candidate positions, respectively. The method may further include determining a target position of the subject from the one or more candidate positions based on the comparison.

In some embodiments, the imaging device may include a holographic projection device. Obtaining target information of the at least part of the subject may include obtaining third scanning data by causing the holographic projection device to image the at least part of the subject using a millimeter wave, and obtaining the target information based on the third scanning data.

According to another aspect of the present disclosure, a system for positioning a subject is provided. The system may include at least one storage device including a set of instructions or programs and at least one storage device including a set of instructions or programs. When executing the set of instructions or programs, the at least one processor may be configured to cause the system to perform obtaining first information of at least part of a subject when the subject is located at a preset position. The first information may include at least a first set of position data of the at least part of the subject. The at least one processor may be configured to cause the system to perform determining, based on the first information, a first position of each of one or more feature points located on the at least part of the subject. The at least one processor may be configured to cause the system to perform obtaining, using an imaging device, second information of the at least part of the subject when the subject is located at a candidate position. The second information may include at least a second set of position data of the at least part of the subject. The at least one processor may be configured to cause the system to perform determining, based on the second information, a second position of each of the one or more feature points. The at least one processor may be configured to cause the system to perform determining a first distance between the first position and the second position for each feature point of the one or more feature points. The at least one processor may be configured to cause the system to perform determining, based at least in part on the one or more first distances, a target position of the subject.

According to still a further aspect of the present disclosure, a system for positioning a subject is provided. The system may include at least one storage device including a set of instructions or programs and at least one processor configured to communicate with the at least one storage device. When executing the set of instructions or programs, the at least one processor may be configured to cause the system to perform obtaining, using an imaging device, target information of at least part of a subject when the subject is located at a preset position. The target information may include at least a set of target position data of the at least part of the subject. The at least one processor may be configured to cause the system to perform generating, based on the target information, a virtual representation of the at least part of the subject. The at least one processor may be configured to cause the system to perform comparing the virtual representation of the at least part of the subject and the at least part of the subject located at each of one or more candidate positions, respectively. The at least one processor may be configured to cause the system to perform determining a target position of the subject from the one or more candidate positions based on the comparison.

According to still a further aspect of the present disclosure, a radiotherapy system is provided. The system may include a radiation assembly configured to emit radiation beam, a table configured to support a subject, a holographic projection device configured to scan a target area including at least part of the subject, and a processor. The processor may be configured to control the radiotherapy system. When executing a set of instructions or programs, the processor may be configured to cause the radiotherapy system to perform controlling the holographic projection device to scan the subject to obtain target information of the subject, the target information including at least a target set of position data of the at least part of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further describable in terms of exemplary embodiments. These exemplary embodiments are describable in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been describable at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assemblies of different levels in ascending order. However, the terms may be displaced by other expressions if they achieve the same purpose.

Figure 2:
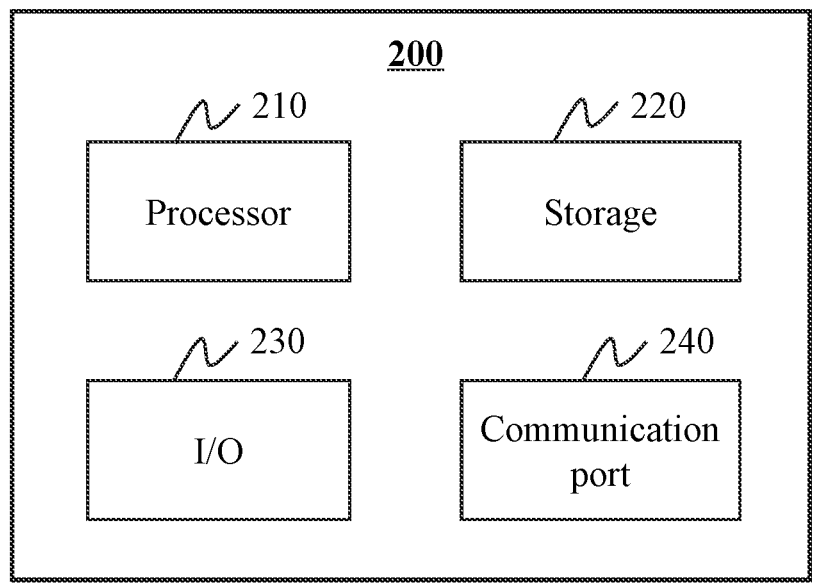
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block describable herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality describable herein may be implemented as software modules/units/blocks, but may be represented in hardware or firmware. In general, the modules/units/blocks describable herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure provides methods and systems for determining the position of a subject with an assistance of a holographic projection device. The methods and systems may be utilized in medical or industrial applications such as disease treatment (such as radiotherapy), disease diagnosis (such as medical imaging), or the like, or any combination thereof. The methods and systems disclosed in the present disclosure may be implemented on a system include a radiotherapy (RT) system, a computed tomography (CT) system, a positron emission tomography (PET) system, a single photon emission computed tomography (SPECT) system, a magnetic resonance imaging (MRI) system, an emission computed tomography (ECT) system, an ultrasonic imaging (UI) system, or the like, or any combination thereof (e.g., a PET-CT system, a PET-MRI system). The following descriptions are provided with reference to an RT system for illustrative purposes and not intended to limit the scope of the present disclosure.

In an aspect of the present disclosure, a target position of a subject may be determined for the delivery of radiotherapy based on scanning data obtained by imaging the subject using a holographic projection device, e.g., a millimeter-wave holographic projection device. For example, a target position may be determined based on a determination whether a first distance between a point of the at least part of the subject (e.g., a region of interest (ROI)) in a preset position and the same point in a candidate position for radiation delivery exceeds a threshold. As another example, a target position may be determined based on an overlapping value between a virtual representation of the at least part of the subject by the holographic projection device and the at least part of the subject. By positioning the subject at the target position, the accuracy of radiation delivery on the ROI may be improved, and the radiation irradiated on normal cells or tissue in the vicinity of the ROI may be reduced.

In some embodiments, a prediction may be made as to whether the subject is going to collide with the radiotherapy device during a radiation delivery based on position data of a target area, including a subject and a motion area of a radiation assembly, and a motion trajectory of the radiation assembly. For example, it may be determined whether at least one distance between the target area and the motion trajectory of the radiation assembly is less than a threshold to make the prediction. Thereby, collision may be prevented during movement of the radiation assembly.

In some embodiments, when a position of the subject is outside a tolerance range, or the subject is going to collide with the radiotherapy device, the position of the subject may be adjusted, and radiation delivery by the radiation assembly may be paused. Thus, the risk of irradiating normal cells may be decreased and the accuracy of radiation delivery and efficacy of radiotherapy may be increased.

Figure 1:
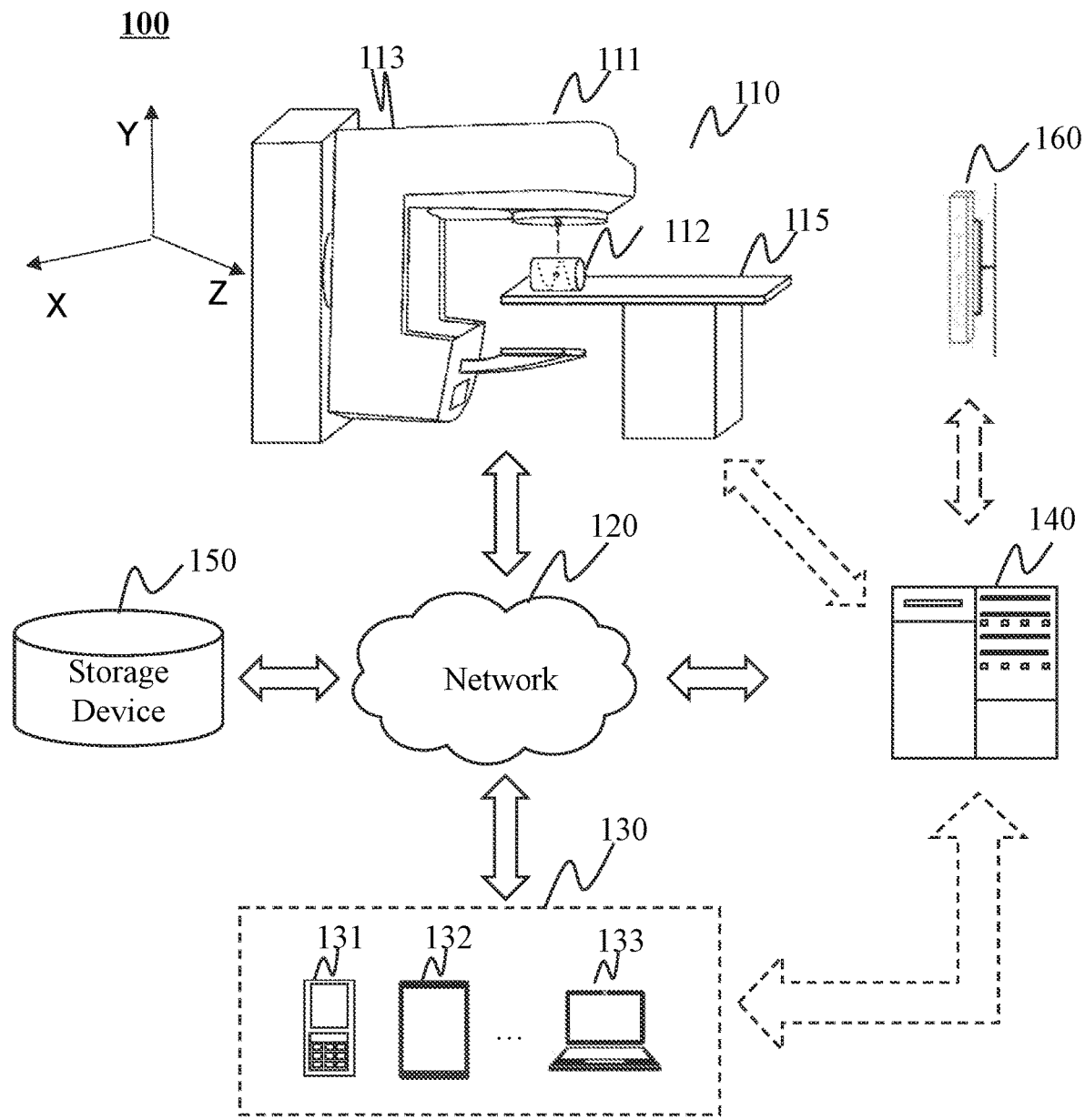
FIG. 1 is a schematic diagram illustrating an exemplary radiotherapy system according to some embodiments of the present disclosure.

FIG. 1 is a schematic diagram illustrating an exemplary RT system 100 according to some embodiments of the present disclosure. The RT system 100 may include a radiotherapy device 110, a network 120, a terminal 130, a processing device 140, a storage device 150, and an imaging device 160. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the radiotherapy device 110, the terminal 130, the storage device 150, and/or the imaging device 160 may be connected to the processing device 140 through the network 120 or directly (e.g., bidirectional connections as indicated by dotted arrows in FIG. 1).

The radiotherapy device 110 may be configured to emit radiations (for example, X-ray, gamma ray, electron ray, proton ray, etc.) towards a subject (e.g., a subject 112 in FIG. 1). The subject may include any biological subject (e.g., a human being, an animal, a plant, or a portion thereof) and/or a non-biological subject (e.g., a phantom). In some embodiments, the radiotherapy device 110 may include an accelerator 111 and a table 115. The accelerator 111 may be a linear accelerator (LINAC), a cyclotron, an electrostatic accelerator, a particle accelerator, a multi-voltage accelerator, etc. The accelerator 111 may generate and emit radiation (e.g., X-ray) to irradiate the subject (e.g., a human being) to kill cancer cells. The accelerator 111 may rotate with a gantry 113. For example, the accelerator 111 may rotate around an axis of the gantry 113 clockwise or counterclockwise to irradiate the subject from various directions within the range of 360°. The table 115 may be configured to support the subject. In some embodiments, the table 115 may be movable. For example, with reference to a three-dimensional coordinate system, the table 115 may move along the directions of x, y, and z axes as shown in FIG. 1. The x-axis and the z-axis shown in FIG. 1 may be horizontal, and the y-axis may be vertical. As illustrated, the positive x direction along the x-axis may be from a right side to a left side of the radiotherapy device 110 seen from the direction facing the front of the radiotherapy device 110; the positive y direction along the y-axis shown in FIG. 1 may be from a lower part to an upper part of the radiotherapy device 110; the positive z-direction along the z-axis shown in FIG. 1 may be from a rear side to a front side of the radiotherapy device 110 seen from the direction facing the front of the radiotherapy device 110. For instance, the table 115 may translate along and/or rotate around the directions of x-axis, y-axis, and z-axis. The table 115 may be moved such that a treatment region of the subject aligns with an isocenter of the radiotherapy device 110 (e.g., the accelerator 111).

The network 120 may include any suitable network that can facilitate the exchange of information and/or data for the RT system 100. In some embodiments, one or more components of the RT system 100 (e.g., the radiotherapy device 110, the terminal 130, the processing device 140, the storage device 150, the imaging device 160, etc.) may communicate information and/or data with one or more other components of the RT system 100 via the network 120. For example, the processing device 140 may obtain scanning data from the radiotherapy device 110 via the network 120. As another example, the processing device 140 may obtain user instructions from the terminal 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
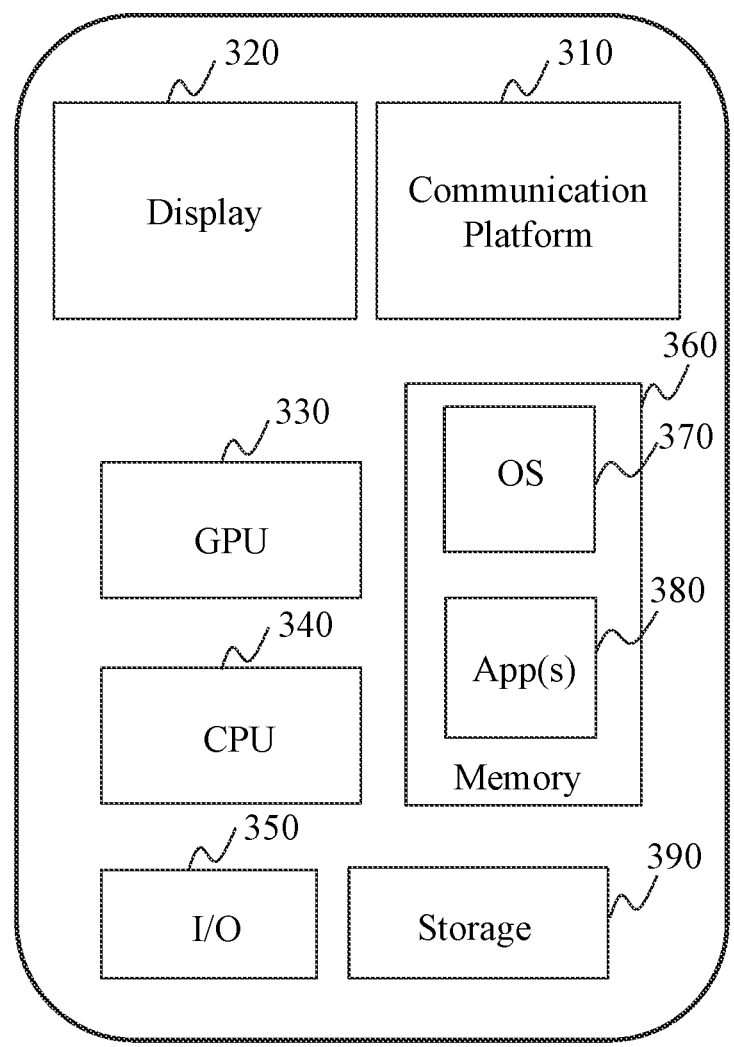
FIG. 3 is a schematic diagram illustrating exemplary hardware and/or software components of an exemplary mobile device according to some embodiments of the present disclosure.

The terminal 130 may enable user interaction between a user and the RT system 100. In some embodiments, the terminal 130 may include one or more devices with data communication, for example, a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal 130 may be part of the processing device 140. In some embodiments, the terminal 130 may include a console from which a user may provide instructions for controlling the radiotherapy system 100, or a portion thereof. The terminal 130 may send an instruction to the radiotherapy system 100 in response to an operation (e.g., click, touch a screen of the terminal 130) of a user (e.g., a doctor).

The processing device 140 may process information obtained from the radiotherapy device 110, the terminal 130, the storage device 150, and/or the imaging device 160. In some embodiments, the processing device 140 may be a single server or a server group. The server group may be centralized or distributed. In some embodiments, the processing device 140 may be local or remote. For example, the processing device 140 may access information stored in the radiotherapy device 110, the terminal 130, the storage device 150, and/or the imaging device 160 via the network 120. As another example, the processing device 140 may be directly connected to the radiotherapy device 110, the terminal 130, the storage device 150, and/or the imaging device 160 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the RT system 100 (e.g., the radiotherapy device 110, the terminal 130, the processing device 140, the imaging device 160). One or more components of the RT system 100 may access the data and/or instructions stored in the storage device 150 via the network 120. In some embodiments, the storage device 150 may be directly connected to or communicate with one or more other components of the RT system 100 (e.g., the radiotherapy device 110, the processing device 140, the imaging device 160). In some embodiments, the storage device 150 may be part of the processing device 140.

The imaging device 160 may be configured to image the subject. In some embodiments, the imaging device 160 may include a charge coupled device (CCD) camera, a laser device, an optical projection system, a holographic projection device, or the like, or any combination thereof. The imaging device 160 may obtain information of the subject (e.g., a patient) prior to the radiotherapy treatment, and/or during the radiotherapy treatment, and the information may include at least a set of position data of the subject. The imaging device 160 may further transmit the information to the processing device 140 for further processing, such as determining one or more feature points. In some embodiments, the imaging device 160 may be calibrated in advance to determine a corresponding relationship between position data of at least part of the subject in a world coordinate system and position data of the at least part of the subject in a camera coordinate system. Thus, scanning data obtained from the imaging device 160 may include position data of the at least part of the subject. Based on the scanning data, a target position of the subject may be determined, a prediction may be made as to whether the subject is going to collide with the radiotherapy device 110 during radiation delivery, and an adjustment of the movement trajectory of the radiotherapy device 110 and/or an adjustment of the movement trajectory of the table 115 may be made if needed.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. Additionally or alternatively, two or more components of the RT system 100 may be integrated into a single component. A component of the RT system 100 may be implemented on two or more sub-components.

FIG. 2 is a schematic diagram illustrating exemplary hardware and/or software components of a computing device 200 according to some embodiments of the present disclosure. The computing device 200 may be used to implement any component of the RT system 100 as describable herein. For example, the processing device 140 and/or the terminal 130 may be implemented on the computing device 200, respectively, via its hardware, software program, firmware, or a combination thereof. Although only one such computing device is shown, for convenience, the computer functions relating to the RT system 100 as describable herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques describable herein. The computer instructions may include, for example, routines, programs, objects, components, data structures, procedures, modules, and functions, which perform particular functions describable herein. For example, the processor 210 may process scanning data obtained from the radiotherapy device 110, the terminal 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is describable in the computing device 200. However, it should be noted that the computing device 200 in the present disclosure may also include multiple processors, thus operations and/or method operations that are performed by one processor as describable in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the RT system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods describable in the present disclosure. For example, the storage 220 may store a program for the processing device 140 to execute to check errors in replanning.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input devices may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the radiotherapy device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, a terminal 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
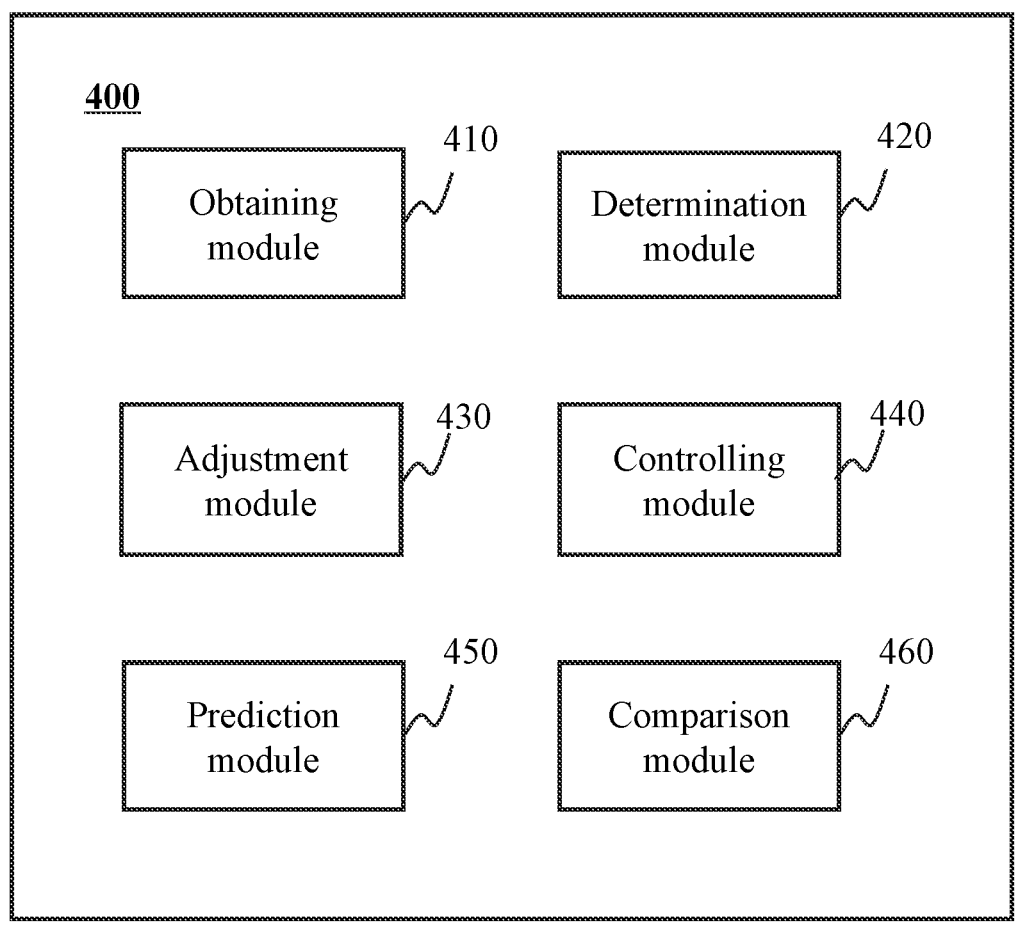
FIG. 4 is a block diagram illustrating an exemplary processing device according to some embodiments of the present disclosure.

FIG. 4 is a block diagram illustrating an exemplary processing device according to some embodiments of the present disclosure. As illustrated in FIG. 4, the processing device 140 may include an obtaining module 410, a determination module 420, an adjustment module 430, a controlling module 440, a prediction module 450, and a comparison module 460.

The obtaining module 410 may be configured to obtain information of at least part of a subject when the subject is located at various positions (e.g., a preset position, one or more candidate positions). In some embodiments, the obtaining module 410 may obtain first information of the at least part of a subject when the subject is located at the preset position. The preset position may refer to a position of the subject when a region to be scanned (e.g., a region of a tumor) of the subject coincides with an isocenter of the radiotherapy device 110. The at least part of the subject may include a region of interest (ROI), and a region at risk associated with the ROI, or the like, or any combination thereof. The first information may include an image (e.g., a three-dimensional (3D) image), position information (e.g., a first set of position data) of the at least part of the subject located at the preset position, or the like, or any combination thereof. In some embodiments, the first set of position data may include coordinates of any points of the at least part of the subject when the subject is located at the preset position. The 3D image (e.g., a virtual representation) may be generated by the imaging device 160 (e.g., a millimeter-wave holographic projection device) performing the holographical projection on the at least part of the subject. In some embodiments, the obtaining module 410 may obtain the first information of the at least part of the subject by imaging the at least part of the subject using the imaging device 160. In some embodiments, the obtaining module 410 may obtain the first information from a storage device (e.g., the storage device 150, the storage 220, and/or the storage 390).

In some embodiments, the obtaining module 410 may obtain the second information of the at least part of the subject using an imaging device 160 when the subject is located at a candidate position. The candidate position may refer to a position at which the subject is located before the subject being exposed to radiation. The second information may include an image (e.g., a 3D image) of the at least part of the subject, position information (e.g., a second set of position data) of the at least part of the subject, or the like, or any combination thereof. In some embodiments, the second information may be obtained based on first scanning data. The obtaining module 410 may obtain the first scanning data by imaging the subject via the millimeter-wave holographic projection device. Similar to the first information, the second information may include an image (e.g., a 3D image) of the at least part of the subject, position information (e.g., a second set of position data) of the at least part of the subject, or the like, or any combination thereof. The second set of position data of the at least part of the subject may include coordinates of any points of the at least part of the subject located at the candidate position. The coordinates of the second set of position data and the coordinates of the first set of position data may be in the same coordinate system.

In some embodiments, the obtaining module 410 may obtain third information of the at least part of the subject using the imaging device (e.g., the holographic projection device using a millimeter wave) during the movement or after the movement of the subject to the adjusted position. Similar to the first information and the second information, the third information may include at least a third set of position data of the at least part of the subject.

In some embodiments, the obtaining module 410 may obtain fourth information of the at least part of the subject using the imaging device 160 (e.g., a millimeter-wave holographic projection device) at a time interval during a radiation session. The radiation session may include a treatment period of multiple days (e.g., 2 to 5 weeks), or a single radiation during the treatment period (e.g., 3 to 10 minutes). The fourth information may include an image (e.g., a 3D image) of the at least part of the subject, position information (e.g., position data) of the at least part of the subject, or the like, or any combination thereof.

In some embodiments, the obtaining module 410 may obtain second scanning data by scanning a target area with the imaging device 160. The target area may include the subject and a motion area of the radiation assembly, for example, the radiotherapy device 110. The motion area may refer to a space occupied by the radiation assembly during movement, a rotation space of the gantry 113 of the radiotherapy device 110, or the like, or a combination thereof. In some embodiments, the obtaining module 410 may obtain fifth information of the target area based on the second scanning data. The fifth information may include an image (e.g., a 3D image) of the at least part of the subject and position information (e.g., a fifth set of position data) of the at least part of the subject, or the like, or any combination thereof. Besides, the obtaining module 410 may obtain a motion trajectory of the radiation assembly. The motion trajectory may be obtained from a therapy planning system (TPS). Based on the coordinate system in which the fifth coordinates are expressed, the plurality of rotation angle-time pairs may be converted into a plurality of coordinate-time pairs. The motion trajectory of the radiation assembly may be represented by a plurality of coordinates (or referred to as the sixth coordinates).

In some embodiments, the obtaining module 410 may obtain target information of at least part of a subject using an imaging device. In some embodiments, the obtaining module 410 may obtain third scanning data by causing the holographic projection device to image the at least part of the subject at the preset position using a millimeter wave. Based on the third scanning data, the target information may include at least position information of the at least part of the subject, an image (e.g., a 3D image) of the at least part of the subject, or the like, or any combination thereof.

The determination module 420 may be configured to determine a first position of each of one or more feature points located on the at least part of the subject based on the first information. In some embodiments, a feature point may be any point located on the ROI or near the ROI (for example, within a preset range around the ROI), a point having a specific characteristic compared to other points located on the ROI of the subject, or the like, or any combination thereof. Since the feature point(s) is/are located on the at least part of the subject, the coordinate(s) of the feature point(s) in the coordinate system may be obtained based on the first set of position data. A position (i.e., the first position) of the feature point may be represented by coordinates (or referred to as the first coordinates) of a feature point in the coordinate system. The first position may also be represented by a distance (or referred to as the preset distance) and/or an orientation (or referred to as the preset orientation) between the feature point and a reference point such as the origin of the coordinate system (e.g., an emission source of the imaging device 160 or an isocenter of the radiotherapy device 110).

In some embodiments, the determination module 420 may determine a second position of each of the one or more feature points based on the second information. The second position of the feature point may be represented by the coordinates (or referred to as the second coordinates) of the feature point, or the distance (or referred to as the candidate distance) and the orientation (or referred to as the candidate orientation) included in the second set of position data.

In some embodiments, the determination module 420 may determine a first distance between the second position and the first position for each feature point of the one or more feature points. The first distance may be determined based on the first coordinates indicating the first position and the second coordinates indicating the second position or the distances (the preset distance and the candidate distance) and the orientations (the preset orientation and the candidate orientation) indicating the first position and the second position.

In some embodiments, the determination module 420 may determine a target position of the subject based on the one or more first distances. The target position of the subject may refer to a position that the subject can receive ray irradiation safely and accurately. During radiotherapy, it is desired that the target position of the subject may coincide with the preset position of the subject or the distance therebetween may be within a tolerable range (or referred to as first threshold). To determine the target position, the determination module 420 may determine whether the first distance is less than the first threshold. If the first distance is less than the first threshold, it may indicate that the candidate position of the subject satisfies a condition for radiation delivery, that is, the candidate position is within the tolerable range of the preset position. The candidate position may be designated as the target position of the subject. If the first distance exceeds the first threshold, it may indicate that the candidate position is not precise enough to act as the target position and needs to be adjusted.

In some embodiments, the determination module 420 may determine a fourth position of each of the one or more feature points based on the fourth information. The fourth position may be indicated by coordinates (or referred to as the fourth coordinates) included in the fourth set of position data and defined by the coordinate system defining the first coordinates, the second coordinates, and the third coordinates. The determination module 420 may determine a third distance between the fourth position and the first position. The determination of the third distance may be the same as that of the first distance. Based on the third distance, the determination module 420 may determine whether the third distance is less than the first threshold to control a radiation assembly to perform a preset operation.

In some embodiments, the determination module 420 may determine at least one fourth distance between the subject and the motion trajectory of the radiation assembly based on the fifth coordinates corresponding to the target area and the sixth coordinates corresponding to the motion trajectory of the radiation assembly. The determination module 420 may determine whether the at least one fourth distance is less than a second threshold to predict whether the subject and the radiation assembly are going to collide.

In some embodiments, the determination module 420 may determine a target position of the subject from the one or more candidate positions based on the comparison (e.g., determining an overlapping degree) of the virtual representation of the at least part of the subject and the at least part of the subject located at one or more candidate positions.

The adjustment module 430 may be configured to adjust the candidate position of the subject to an adjusted position such that a second distance between a third position of each of the one or more feature points and the first position of the each feature point is less than the first threshold. To adjust the candidate position, a relative orientation (or referred to as the first relative orientation) between the second position and the first position, and a length of a projection line between the second position and the first position may be determined. Based on the first relative orientation and the length of the projection line, the adjustment module 430 may adjust the position of the table 115 to adjust the candidate position of the subject. The adjustment module 430 may also adjust a position of the subject based on a prediction result of whether the subject and the radiation assembly are going to collide.

In some embodiments, the adjustment module 430 may cause the table 115 to move to adjust the position of the subject according to a control instruction entered by a user (e.g., a doctor). In some embodiments, the user (e.g., a doctor) may also manually adjust the position of the table 115 based on results (e.g., the first relative orientation) determined by the adjustment module 430.

The controlling module 440 may be configured to cause a radiation assembly to perform a preset operation corresponding to the third distance based on a third distance between the fourth position and the first position of each of the one or more feature points. The preset operation of the radiation assembly may include an operation of continuing to emit radiation beams, an operation of stopping emitting radiation beams, or the like. The controlling module 440 may control the radiation assembly to continue to emit radiation beams on the at least part of the subject based on a determination result that the third distance is less than the first threshold. The controlling module 440 may immediately cause the radiation assembly to stop emitting radiation beams, and adjust the table 115 to make the subject in the correct position based on a determination result that the third distance exceeds the first threshold.

The prediction module 450 may be configured to predict whether the subject and the radiation assembly are going to collide based on the fifth information and the motion trajectory. A prediction result of whether the subject and the radiation assembly are going to collide may be generated based on one or more distances between the moving radiation assembly and the subject (or referred to as the fourth distances). At least one fourth distance may be determined based on the fifth coordinates corresponding to the target area and the sixth coordinates corresponding to the motion trajectory of the radiation assembly. The prediction module 450 may generate the prediction result that the subject and the radiation assembly are going to collide based on a determination result that the at least one fourth distance is less than a second threshold.

In some embodiments, the prediction module 450 may generate a virtual representation of the at least part of the subject based on the target information. In some embodiments, the virtual representation may be displayed in the preset position.

The comparison module 460 may be configured to compare the virtual representation of the at least part of the subject and the at least part of the subject located at one or more candidate positions, respectively. The comparison module 460 may compare the virtual representation of the at least part of the subject and the at least part of the subject at the candidate position to determine an overlapping value. The overlapping value may indicate an overlapping degree of the virtual representation of the at least part of the subject and the at least part of the subject.

More detailed descriptions of the modules in the processing device 140 may be found in elsewhere of the present disclosure, for example, the descriptions of FIGS. 5-8.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. Additionally or alternatively, two or more modules may be integrated into a single module and/or a module may be divided into two or more units. However, those variations and modifications also fall within the scope of the present disclosure.

Figure 5:
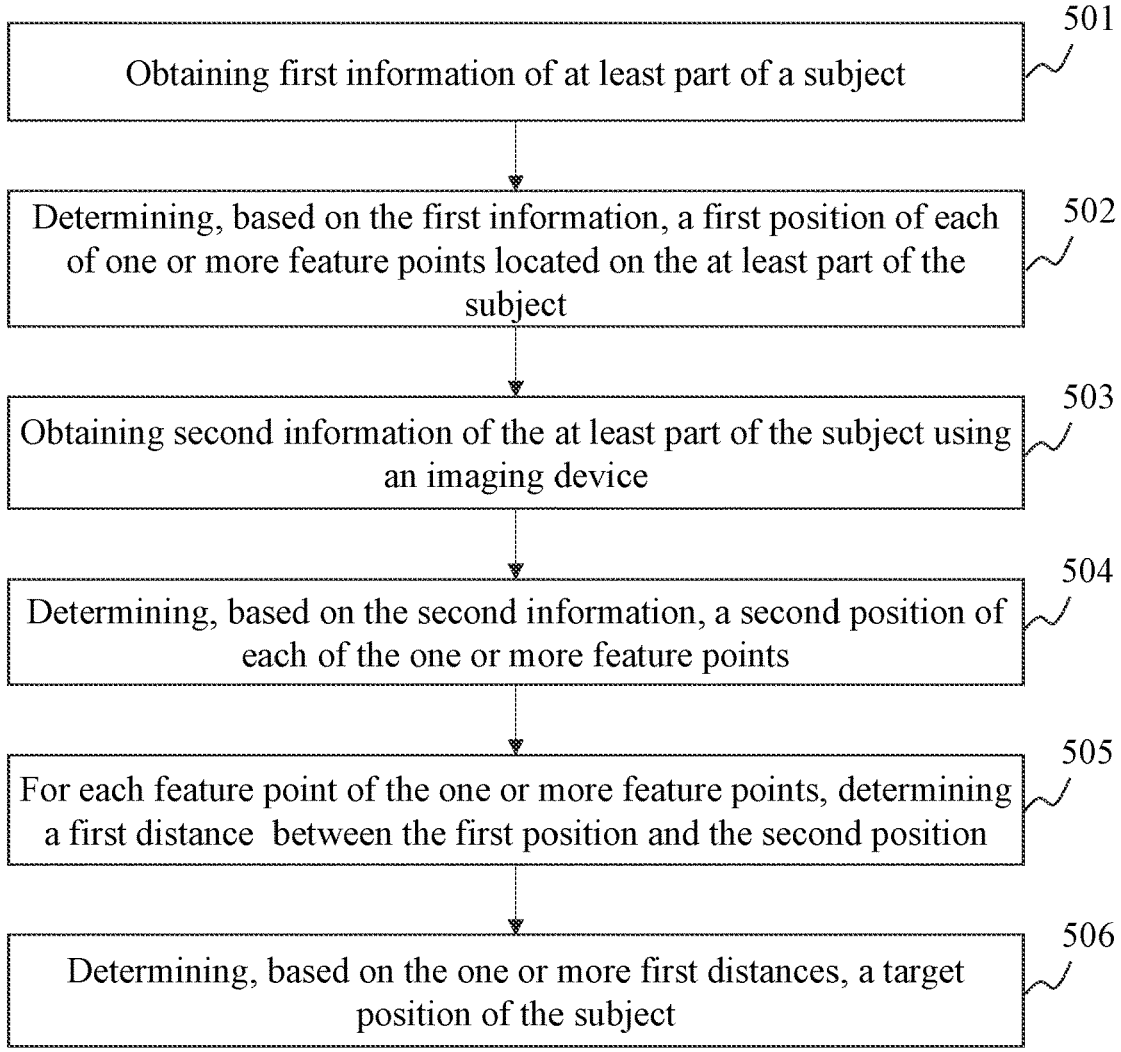
FIG. 5 is a flowchart illustrating an exemplary process for determining a target position of a subject according to some embodiments of the present disclosure.

FIG. 5 is a flowchart illustrating an exemplary process for determining a target position of a subject according to some embodiments of the present disclosure. In some embodiments, process 500 may be executed by the RT system 100. For example, the process 500 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 500.

In 501, the processing device 140 (e.g., the obtaining module 410) may obtain first information of at least part of a subject. In some embodiments, the subject may include a patient to be treated, a phantom for calibration, an industrial material to be tested, or the like, or any combination thereof. The subject may be placed on a table (e.g., the table 115) in a posture. For example, the subject may be supine, prone, or latericumbent on the table. In some embodiments, the subject may be located at a preset position. The preset position may refer to a position of the subject when a region to be scanned (e.g., a region of a tumor) of the subject coincides with an isocenter of the radiotherapy device 110. In some embodiments, the isocenter of the radiotherapy device 110 may be fixed. The preset position may be determined based on the isocenter of the radiotherapy device 110. The following may be an illustrative description for determination of the preset position. After the subject is placed on the table 115, the subject may be imaged, such as using Computed Tomography (CT), to obtain a CT image of the subject. A position of the region to be scanned (e.g., a region of a tumor) may be determined based on the CT image of the subject. Thereafter, by shining a laser light on the subject, one or more markers may be identified on a surface of the subject (e.g., a surface of a patient), for example, three markers. The marker(s) may be labeled as one or more of any shapes, such as a cross, a dot, or the like, or any combination thereof. Therefore, a central point of a treatment region (i.e., the region to be scanned described above) may be determined according to the one or more markers, such as using an approach of determining a central point of a polygon formed by the one or more markers. After the central point of the treatment region is determined, the table 115 may be moved to a position based on the marker(s) at which the central point of the treatment region coincides with the isocenter (also referred to as a machine isocenter) of the radiotherapy device 110. The position of the table 115 may be referred to as a treatment position of the table 115, and a position of the subject on the table 115 when the table 115 is located at the treatment position may be referred to as the preset position. The above process may also be known as radiotherapy localization. The preset position may be the position of the subject to receive radiotherapy treatment. In some embodiments, the at least part of the subject may include a region of interest (ROI), and a region at risk associated with the ROI, or the like, or any combination thereof. The ROI may include a region of a tumor (e.g., a region to be scanned), a region at risk including an organ or tissue at risk in the vicinity of the region of the tumor, or the like, or any combination thereof. The region at risk associated with the ROI may include a region of an organ or tissue at risk in the vicinity of the tumor, a region in the vicinity of the organ or tissue at risk), or the like, or any combination thereof. As used herein, an organ or tissue at risk may be the organ or tissue subject to radiation targeted at the ROI due to its vicinity to the ROI.

In some embodiments, the first information of the at least part of the subject may be obtained by imaging the at least part of the subject using the imaging device (e.g., the imaging device 160). In some embodiments, the imaging device 160 may be a holographic projection device, e.g., a millimeter-wave holographic projection device. The holographic projection imaging technology is a 3D imaging technique that uses the principles of interference and diffraction to produce an image of a subject. And the millimeter-wave holographic projection device may have advantages including, e.g., high spatial resolution, and/or high penetrability. In addition, a millimeter wave may have a strong penetrating capacity, and thus may penetrate smoke, dust, fog, etc., and work in various indoor environments. Therefore, the millimeter-wave holographic projection on the subject may have a good resolving power for the surface color of the subject (for example, skin color), things on the surface of the subject (e.g., markers, clothes, etc.), etc. As used herein, the resolving power refers to an ability of an imaging device (e.g., the millimeter-wave holographic projection device) to separate (i.e., to see as distinct) points of an object (e.g., the subject) that are located at a small angular distance. The obtained information (e.g., the first information) of the subject may be clear and accurate, and effectively describe the surface of the subject. In some embodiments, the imaging device 160 may emit a millimeter wave toward the at least part of the subject and receive at least a portion of the millimeter wave reflected from the subject. By processing the reflected millimeter wave detected by the imaging device 160, the first information of at least part of the subject may be obtained.

In some embodiments, the obtaining module 410 may obtain the first information from a storage device (e.g., the storage device 150, the storage 220, and/or the storage 390). At least a portion of the first information may be stored in the storage device in advance, and the obtaining module 410 may access the storage device to retrieve the at least a portion of the first information. For example, after the subject is positioned (e.g., using a radiotherapy simulator), or the subject (e.g., a patient) is undergoing radiotherapy treatment, the imaging device 160 (e.g., the millimeter-wave holographic projection device) may perform a holographical projection to obtain the first information, and store the first information in the storage device.

In some embodiments, the first information may include an image (e.g., a 3D image) of the at least part of the subject, position information (e.g., a set of position data) of the at least part of the subject, or the like, or any combination thereof. In some embodiments, the first information may include at least a first set of position data of the at least part of the subject. For example, the first set of position data may include one or more coordinates, angles, etc., that can represent the position of the at least part of the subject. In some embodiments, the first set of position data of the at least part of the subject may include coordinates of any points of the at least part of the subject when the subject is located at the preset position. These coordinates may be with respect to a coordinate system. The coordinate system may be a three-dimensional coordinate system including a camera coordinate system, a 3D Cartesian coordinate system (i.e., an orthogonal coordinate system), a spherical polar coordinate system, a cylindrical coordinate system, or the like. For example, the camera coordinate system may use an optical center of the imaging device 160 as an origin, the optical axis of the imaging device 160 may be determined as a z-axis, and an xoy plane may be parallel to an image plane. Taking the 3D Cartesian coordinate system as an example, the origin o of the coordinate system may be the emission source of the imaging device 160. Two mutually perpendicular lines in the horizontal plane intersecting at the emission source may be designated as the x-axis and the y-axis, respectively. And a line passing through the emission source and perpendicular to the horizontal plane may be designated as the z-axis. As a further example, the origin o of the coordinate system may be the isocenter of the radiotherapy device 110. The two mutually perpendicular straight lines in the horizontal plane intersecting at the isocenter of the radiotherapy device 110 may be designated as the x-axis and the y-axis, respectively. And a line passing through the isocenter of the radiotherapy device 110 and perpendicular to the horizontal plane (i.e., a xoy plane) may be designated as the z-axis. In some embodiments, the coordinate system may also be a coordinate system established based on a space where the radiotherapy system 100 exists. In some embodiments, a coordinate may indicate position information of a spatial point, e.g., a point of the at least part of the subject. The position information of a point may include a relative position to a reference point, such as the emission source or the isocenter of the imaging device 160, a distance and/or an orientation between the point and the reference point. In some embodiments, after obtaining the first information, the obtaining module 410 may transmit the obtained first information to a storage device for storage, for example, the storage device 150, or the storage device 220. In some embodiments, after obtaining the first information, the obtaining module 410 may transmit the obtained first information to one or more other components of the radiotherapy system 100, e.g., the terminal 130, the processing device 140, etc., for further processing and/or display.

In some embodiments, the first information may also include the 3D image of the at least part of the subject. For instance, after performing the holographical projection on the at least part of the subject, the imaging device 160 (e.g., a millimeter-wave holographic projection device) may generate a 3D image based on the reflected wave, and transmit the 3D image to the processing device 140 (or the obtaining module 410). Compared with an image obtained using a traditional imaging technique (e.g., a photoacoustic imaging technique, a magnetic resonance imaging, etc.), the 3D image may have a high definition, a high contrast, and a brighter color. In some embodiments, the 3D image may be represented in the real world by the imaging device 160. For example, the imaging device 160 (or the holographic projection device) may reproduce a virtual representation of the at least part of the subject. The virtual representation may include the size and/or shape of the at least part of the subject. In addition, the virtual representation may be reproduced at any location, for example, the preset position at which the subject is located, or any position of the space where the radiotherapy system 100 exists. For instance, the virtual representation may be superimposed on the subject to mimic the at least part of the subject that is inside the subject.

In 502, the processing device 140 (e.g., the determination module 420) may determine a first position of each of one or more feature points located on the at least part of the subject based on the first information. In some embodiments, the feature point may be any point located on the ROI or near the ROI, for example, within a preset range around the ROI. In some embodiments, the feature point may be a point having a specific characteristic compared to other points located on the ROI of the subject. For example, the feature point may be a point relatively immobile, a point easy to be labeled, a point located at a boundary of the ROI, or the like, or any combination thereof. Merely by way of illustration, if the ROI is the head of a patient, the one or more feature points may be a tip of the nose, a lower point of the chin, a raised point of the supra-orbital bone, a raised point of the cheekbone, or the like, or any combination thereof. In some embodiments, the feature point(s) may include at least a point determined in advance. For example, when the subject is being positioned, one or more points on the surface of the at least part of the subject may be labeled, and the labeled one or more points may be designated as the feature points. In some embodiments, the feature point may be labeled using at least the marker(s) described in 501, for example, the three "+" markers. The markers may indicate the ROI of the subject (e.g., the region to be scanned, or the region of the tumor). The ROI of the subject (e.g., the region to be scanned, or the region of the tumor) is the main dose-bearing region during radiotherapy. And the ROI needs to be aligned with the isocenter of a radiotherapy device (e.g., the radiotherapy device 110). Thus, choosing the marker(s) as the feature point(s) may facilitate the positioning of the ROI of the subject during the subsequent operation of process 500.

In some embodiments, the first position of each of the feature points may be determined based on the first information of at least part of the subject. The first set of position data included in the first information may indicate the first position of each of the feature points. Since the feature point(s) is/are located on the at least part of the subject, the coordinate(s) of the feature point(s) in the coordinate system may be obtained based on the first set of position data. Therefore, the coordinates of a feature point (or referred to as the first coordinates) may indicate a position of the feature point in the coordinate system. The position may be referred to as the first position, and the first position may be represented by the first coordinates. Meanwhile, the first coordinates may indicate a distance and/or an orientation between the feature point and a reference point such as the origin of the coordinate system (e.g., the emission source of the imaging device 160 or the isocenter of the radiotherapy device 110). So, the first position may also be represented by the distance (or referred to as the preset distance) and the orientation (or referred to as the preset orientation), or combined with the first coordinates.

In 503, the processing device 140 (e.g., the obtaining module 410) may obtain second information of the at least part of the subject using an imaging device (e.g., the imaging device 160). The second information of the at least part of the subject may be obtained when the subject is located at a candidate position. In some embodiments, the candidate position may refer to a position at which the subject is located before the subject being exposed to radiation. For example, when radiation is going to be delivered to the subject (e.g., a patient) (e.g., radiotherapy after radiotherapy localization, or different treatment sessions of radiotherapy), the patient may need to lie on the table 115 in the same posture (e.g., the posture mentioned in operation 501) by performing the radiotherapy localization. The table 115 may be moved to a position close to or coincide with the treatment position, and a position of the subject on the table 115 may be referred to as the candidate position.

In some embodiments, the imaging device (e.g., the imaging device 160) may include a holographic projection device. The processing device 140 may cause the holographic projection device to image the subject using, e.g., a millimeter wave, to obtain first scanning data, and further obtain the second information based on the first scanning data. Similar to a traditional imaging device, the first scanning data may include raw projection data of the at least part of the subject, and an image of the at least part of the subject may be obtained based on the raw projection data by performing an imaging reconstruction operation. Further, the first scanning data may include information carried by reflected waves that are detected by the holographic projection device. Position information of objects (e.g., the at least part of the subject) encountered during the wave propagation may be recorded in the reflected waves. Thus, the second information may include an image (e.g., a 3D image) of the at least part of the subject and/or position information (e.g., a second set of position data) of the at least part of the subject. In some embodiments, the second information may be similar to the first information. The second information may include at least a second set of position data of the at least part of the subject. The second set of position data of the at least part of the subject may include coordinates of any points of the at least part of the subject when the subject is located at the candidate position. And the coordinates in the second set of position data may be with respect to the same coordinate system as the first set of position data. The second information may also include a 3D image of the at least part of the subject that can virtually represent the subject or a portion thereof, e.g., the at least part of the subject. The coordinates and the 3D image may be similar to those described in 501, which are not repeated here.

In 504, the processing device 140 (e.g., the determination module 420) may determine a second position of each of the one or more feature points based on the second information. Since the feature point(s) has been determined, the determination module 420 may directly determine the second position of each of the one or more feature points based on the second information. Similar to the first position of a feature point, the second position of the feature point may be represented by the coordinates (or referred to as the second coordinates) of the feature point included in the second set of position data. Similarly, the second coordinates may indicate a distance and/or an orientation between the feature point and a reference point such as the origin of the coordinate system (e.g., the millimeter wave emission source of the imaging device 160 or the isocenter of the radiotherapy device 110). So, the second position of the feature point may also be represented by the distance (or referred to as the candidate distance) and the orientation (or referred to as the candidate orientation) indicated by the second coordinate, or combined with the second coordinates. A same reference point may be used in describing the first position and the second position.

In 505, for each feature point of the one or more feature points, the processing device 140 (e.g., the determination module 420) may determine a first distance between the second position and the first position. In some embodiments, the first distance between the second position and the first position may include a spatial distance therebetween (or referred to as a first spatial distance). The first distance may be determined based on the first coordinates indicating the first position and the second coordinates indicating the second position. Assuming that the first coordinates indicating the first position of the feature point is $(x_1, y_1, z_1)$, and the second coordinates indicating the second position of the feature point is $(x_2, y_2, z_2)$, the first distance may be determined as follows:

$$|d| = \sqrt{(x_1-x_2)^2 + (y_1-y_2)^2 + (z_1-z_2)^2}. \quad (1)$$

The determination module 420 may obtain the first difference between the first position and the second position according to the equation (1). In some embodiments, the first distance may be determined based on the distances (the preset distance and the candidate distance) and the orientations (the preset orientation and the candidate orientation) indicating the first position and the second position. Taking the example of the reference point as the emission source, assume that a distance (denoted as AO) from the first position (denoted as A) to the reference point (denoted as O) is a, and a distance (denoted as BO) from the second position (denoted as B) to the reference point is b. An angle (denoted as $\delta$) between the AO and the BO may be determined as follows:

$$\delta = \arccos a/b. \quad (2)$$

The first distance between the first position and the second position may be determined as follows:

$$c = \sqrt{a^2 + b^2 - 2ab\cos\delta}. \quad (3)$$

In 506, the processing device 140 (e.g., the determination module 420) may determine a target position of the subject based on the one or more first distances. The target position of the subject may refer to a position that the subject can receive ray irradiation safely and accurately. Radiation can not only kill tumor cells but also damage normal cells. Hence, during radiotherapy, it is desired that the ROI of the subject (e.g., the region to be scanned, or the region of the tumor) coincide with an irradiation area of the radiotherapy device 110, or a deviation between the ROI and the irradiation area is within a tolerable range. It may improve the accuracy of radiation irradiated on the ROI and reduce the radiation irradiated on normal cells or tissue in the vicinity of the ROI. When the deviation exceeds a tolerable range (for example, the deviation >10 mm), an unacceptable or dangerous amount of radiation may be irradiated on normal cells or tissue in the vicinity of the ROI, causing damages to and side effects on such normal cells or tissue. Therefore, it is important to determine a precise target position of the subject, which may provide guidance to subsequent operations to be performed on the subject, for example, to continue radiotherapy or to perform position adjustment of the subject. In some embodiments, the target position of the subject may coincide with the preset position of the subject or the distance therebetween may be within a tolerable range (or referred to as first threshold). In some embodiments, the first threshold may be a value according to a default setting of the radiotherapy system 100, such as 0.5 mm, 1 mm, 1.5 mm, 2 mm, etc. In some embodiments, the first threshold may be adjusted under different situations or specified by a user. To determine the target position, the determination module 420 may determine whether the first distance is less than the first threshold. The determination module 420 may compare the first distance with the first threshold. If the first distance is less than the first threshold, it may indicate that the candidate position of the subject satisfies a condition for radiation delivery, that is, the candidate position is within the tolerable range of the preset position. The candidate position may be designated as the target position of the subject. The radiation may be delivered to the ROI of the subject. At this point, the subject may be ready to receive radiation. If the first distance is greater than the first threshold, it may indicate that the candidate position of the subject does not satisfy the condition for radiation delivery, that is, the candidate position is outside the tolerable range of the preset position. If the subject located at the candidate position is subject to radiation, undesirable or tolerable damages and/or side effects may occur. Thus, the candidate position of the subject may need to be adjusted according to processes disclosed herein. See, e.g., FIG. 6 and description thereof.

In some embodiments, when the first distance exceeds the first threshold, it may indicate that the candidate position is not precise enough to act as the target position. The processing device 140 (e.g., the adjustment module 430) may adjust the candidate position of the subject to an adjusted position such that a second distance between a third position of each of the one or more feature points and the first position of the each feature point is less than the first threshold. The third position may be obtained based on third information of the at least part of the subject, and the third information may include at least a third set of position data of the at least part of the subject. To adjust the candidate position, the adjustment module 430 may determine a relative orientation (or referred to as the first relative orientation) between the second position and the first position, and adjust the position of the table 115 along the first relative orientation to adjust the candidate position of the subject. In some embodiments, the first relative orientation may be determined based on the coordinates (e.g., the first coordinates and the second coordinates) of the feature point. Assuming that the first coordinate of the feature point (denoted as A) is $(x_1, y_1, z_1)$, and the second coordinate (denoted as B) is $(x_2, y_2, z_2)$. Thus, the adjustment module 430 may determine a length $|d'|$ of a projection line of line AB in the xoy plane (e.g., a horizontal plane) as follow:

$$|d'|=\sqrt{(x_1-x_2)^2+(y_1-y_2)^2}. \quad (4)$$

Then, an angle θ between line AB and the projection line of line AB may be determined as:

$$\theta=\arccos|d'|/|d|. \quad (5)$$

The angle θ may be used to represent the first relative orientation with respect to the horizontal plane. It should be noted that the relative orientation may be represented as in different forms. The above examples are merely provided for illustration purposes and not intended to limit the scope of protection of the present disclosure. After determining the first relative orientation, the adjustment module 430 may generate a control instruction based on the first relative orientation and the table 115 may be configured to automatically move according to the control instruction to adjust the position of the subject. For example, according to the control instruction, the table 115 may rotate by the first relative orientation. An angle between the moving direction and the horizontal plane may be θ, and a movement distance may be |d'|. During the movement or after the movement (e.g., when the subject is moved to the adjusted position), the processing device 140 may obtain third information of the at least part of the subject using the imaging device (e.g., the holographic projection device using a millimeter wave). The third information may include at least a third set of position data of the at least part of the subject. Also, the third information may be similar as to the first information and the second information. The third position of each of the one or more feature points may also be indicated by coordinates (or referred to as the third coordinates) with respect to the same coordinate system as the first coordinates and the second coordinates. The adjustment module 430 may determine the second distance between the third position of each of the one or more feature points and the first position of the each feature point based on the third coordinates and the first coordinates. If the second distance is less than the first threshold, the table 115 may stop moving. The adjusted position of the subject satisfies the condition for radiation delivery, and may be designated as the target position of the subject. If the second distance is greater than the first threshold, the table 115 may continue to move, until the second distance is less than the first threshold. In some embodiments, the adjustment module 430 may cause the table 115 to move to adjust the position of the subject according to a control instruction entered by a user (e.g., a doctor). In some embodiments, the user (e.g., a doctor) may also manually adjust the position of the table 115 based on results determined by the adjustment module 430 (e.g., the first relative orientation).

It should be noted that the above description of the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, if the first distance and/or the second distance are equal to the first threshold, it may be deemed that the candidate position/third position is within the tolerable range of the preset position or does not satisfy the condition for radiation delivery. How to handle the situation that the first distance and/or the second distance are equal to the first threshold may be decide by a user (e.g., a doctor) or set in advance according to different situations.

Figure 6:
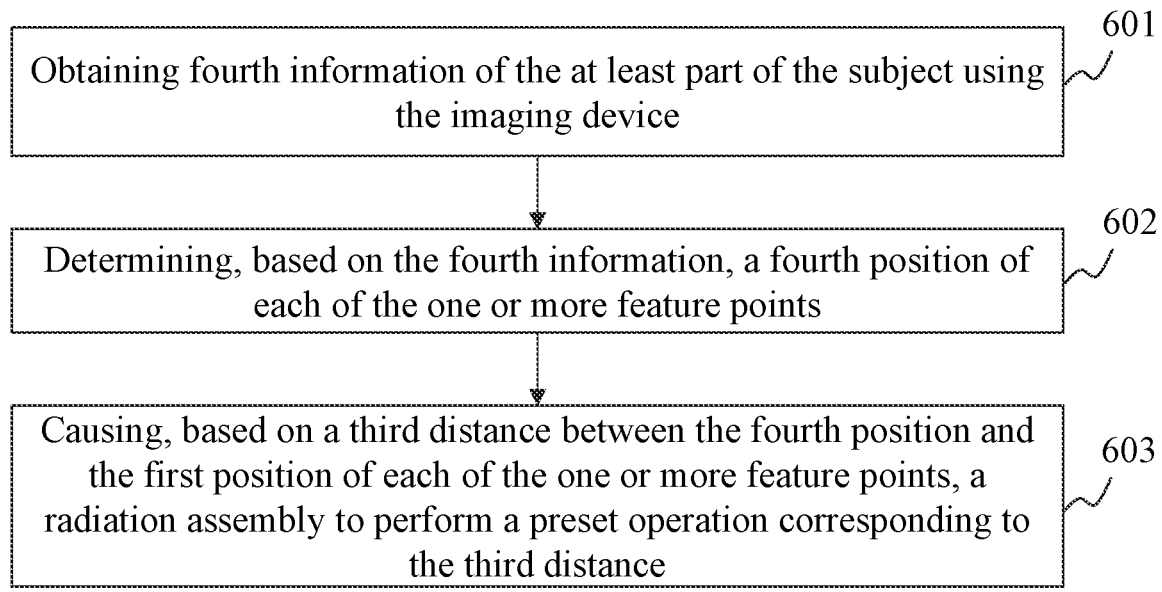
FIG. 6 is a flowchart illustrating an exemplary process for controlling a radiation assembly according to some embodiments of the present disclosure.

FIG. 6 is a flowchart illustrating an exemplary process for controlling a radiation assembly according to some embodiments of the present disclosure. In some embodiments, process 600 may be executed by the RT system 100. For example, the process 600 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 600.

When a subject (e.g., a patient) is subjected to a radiotherapy treatment, the position of the patient, and/or the position of the ROI may change. For example, a position movement may occur due to the subject movement when the subject feels uncomfortable or breathes. It may cause the ROI of the subject to deviate from the isocenter of the radiotherapy device 110. Thus, it is desirable to control the radiation delivery by the radiotherapy device 110 by monitoring the target position of the subject in real-time during radiation delivery, thereby decreasing the risk of irradiating normal cells and increasing the accuracy of radiation delivery and efficacy of radiotherapy.

In 601, the processing device 140 (e.g., the obtaining module 410) may obtain fourth information of the at least part of the subject using the imaging device at a time interval during a radiation session. In some embodiments, the time interval may be a default value of the radiotherapy system 100, such as 0.5 seconds, 1 second, 2 seconds, etc., or may be adjusted under different application scenarios. The radiation session may include a treatment period of multiple days (e.g., 2 to 5 weeks), or a single radiation during the treatment period (e.g., 3 to 10 minutes). The fourth information may be obtained using the imaging device 160 (e.g., a millimeter-wave holographic projection device). For example, the fourth information may be obtained by performing holographic projection on the subject. Similar to the first information, the second information, and the third information, the fourth information may be obtained through data processing and image reconstruction. The fourth information may include an image (e.g., a 3D image) of the at least part of the subject, position information (e.g., position data) of the at least part of the subject, or the like, or any combination thereof. The fourth information may include at least a fourth set of position data of the at least part of the subject. In some embodiments, the obtaining module 410 may communicate with the imaging device 160 to obtain the fourth information.

In 602, the processing device 140 (e.g., the determination module 420) may determine a fourth position of each of the one or more feature points based on the fourth information. Similar to the first position, the second position, and third position, the fourth position of each feature point may be obtained from the fourth information. The fourth position may be indicated by coordinates (or referred to as the fourth coordinates) included in the fourth set of position data and defined by the coordinate system defining the first coordinates, the second coordinates, and the third coordinates. For example, the coordinate system may use the emission source of the imaging device 160 as the origin, or use the isocenter of the radiotherapy device 110 as the origin.

In 603, the processing device 140 (e.g., the controlling module 440) may cause a radiation assembly to perform a preset operation corresponding to the third distance based on a third distance between the fourth position and the first position of each of the one or more feature points. The radiation assembly may include at least a radiation device, for example, the radiotherapy device 110. The preset operation of the radiation assembly may include an operation of continuing to emit radiation beams, an operation of stopping emitting radiation beams, or the like. In some embodiments, the determination module 420 may determine a third distance between the fourth position and the first position. The third distance may include a spatial distance. The determination of the third distance may be the same as that of the first distance with reference to the operation 503 in the process 500, and details may not be described herein again. Based on the third distance, the determination module 420 may determine whether the third distance is less than the first threshold. If the third distance is less than the first threshold, it may indicate that the subject is located at a correct position where the radiation will not be delivered out of the range of the ROI of the subject. In other words, the position of the subject during irradiation may be within the tolerance range. Within the tolerance range, the subject may receive the radiation without causing other problems. Thus, the controlling module 440 may control the radiation assembly to continue to emit radiation beams on the at least part of the subject. If the third distance exceeds the first threshold, it may indicate that the position of the subject has been out of the tolerance range. Thus, further radiation on the subject may cause other problems. For example, if radiation continue to be delivered on a subject (e.g., a patient) in an incorrect position, it may cause side effects such as toxicity, and normal cells may be damaged or even killed. In this case, the controlling module 440 may immediately cause the radiation assembly to stop emitting radiation beams, and adjust the table 115 to make the subject in the correct position. In some embodiments, the determination module 420 may determine a relative orientation (or referred to as the second relative orientation) from the fourth position to the first position, and adjust the position of the table 115 along the second relative orientation to adjust the position of the subject. The process of adjustment may refer to operation 506 in the process 500, and details are not described herein again. In some embodiments, the adjustment operation may also be performed manually. For example, the table 115 is moved by a user-input command or directly by manual operation. After the adjustment is completed, the controlling module 440 may control the radiation assembly to emit radiation beams on the at least part of the subject again.

It should be noted that the above description of the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, if the third distance is equal to the first threshold, it may be determined that the radiation assembly may continue to emit radiation beams or stop emitting radiation beams. How to handle the situation when the third distance is equal to the first threshold may be decide by a user (e.g., a doctor) or set in advance according to different situations.

Figure 7:
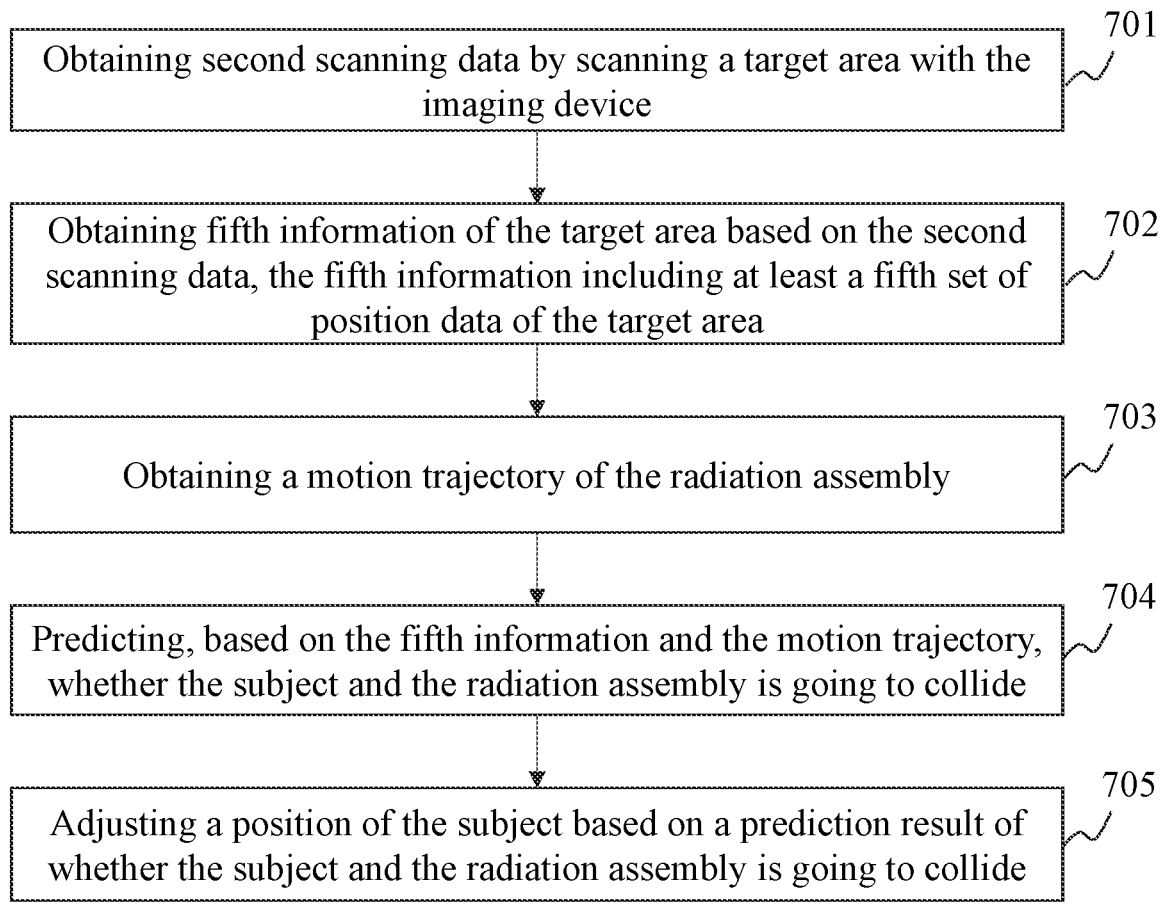
FIG. 7 is a flowchart illustrating an exemplary process for predicting the motion between the subject and a radiation assembly according to some embodiments of the present disclosure.

FIG. 7 is a flowchart illustrating an exemplary process for predicting motion between the subject and a radiation assembly according to some embodiments of the present disclosure. In some embodiments, process 700 may be executed by the RT system 100. For example, the process 700 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 700.

The radiation assembly may include the accelerator 111, the gantry 113, and/or an electronic portal imaging device (EPID). Portions of the radiation assembly may move during a radiation delivery. For example, the accelerator 111 may rotate around an axis of the gantry 113 clockwise or counterclockwise to irradiate the subject from various directions within the range of 360°. Collision may occur during movement. Hence, a distance between the subject and the moving portions of the radiation assembly may be determined to predict whether the radiation assembly (or a portion thereof) is going to collide with the subject.

In 701, the processing device 140 (e.g., the obtaining module 410) may obtain second scanning data by scanning a target area with the imaging device 160. The target area may include the subject and a motion area of the radiation assembly, for example, the radiotherapy device 110. The motion area may refer to a space occupied by the radiation assembly during movement, a rotation space of the gantry 113 of the radiotherapy device 110, or the like, or a combination thereof. The radiation assembly may be located in the motion area when the second scanning data are acquired. In some embodiments, the imaging device may be a holographic projection device. For instance, the imaging device may be a millimeter-wave holographic projection device configured to scan the target area using a millimeter wave to obtain the second scanning data. Similar to the first scanning data, the second scanning data may at least include raw projection data of the target area, and position information of the target area. The second scanning data may be stored in the storage device (e.g., the storage device 150) or an external source for further use.

In 702, the processing device 140 (e.g., the obtaining module 410) may obtain fifth information of the target area based on the second scanning data. In some embodiments, the fifth information of the target area may be obtained by performing data processing and/or image reconstruction on the second scanning data. The fifth information may include an image of the at least part of the subject and position information of the at least part of the subject, or the like, or any combination thereof. The fifth information may include at least a fifth set of position data of the target area. In some embodiments, the fifth set of position data of the target area may be obtained by performing data processing on the second scanning data, such as coordinate transformation. Each point of a plurality of points of the target area may be assigned coordinates (or referred to as the fifth coordinates). The fifth coordinate may be defined by, for example, a 3D Cartesian coordinate system established with the isocenter of the radiation assembly (e.g., the radiotherapy device 110) as the origin. In some embodiments, the fifth information may include a 3D image of the target area. The 3D image of the target area may be obtained by performing image reconstruction on the second scanning data.

In 703, the processing device 140 (e.g., the obtaining module 410) may obtain a motion trajectory of the radiation assembly. In some embodiments, the motion trajectory may be obtained from a therapy planning system (TPS). The TPS refers to a medical device that can simulate a radiotherapy plan by modeling the radiation assembly and the subject. The motion trajectory of the radiation assembly may be obtained from the radiotherapy plan, including a set of position data of the radiation assembly at any time point during radiation delivery (or referred to as the sixth set of position data). Via a direct or indirect communication with the TPS, the obtaining module 410 may obtain the motion trajectory of the radiation assembly. In some embodiments, the sixth set of position data may be represented by a plurality of rotation angle-time pairs. Based on the coordinate system in which the fifth coordinates are expressed, the plurality of rotation angle-time pairs may be converted into a plurality of coordinate-time pairs. The motion trajectory of the radiation assembly may be represented by a plurality of coordinates (or referred to as the sixth coordinates).

In 704, the processing device 140 (e.g., the prediction module 450) may predict whether the subject and the radiation assembly are going to collide based on the fifth information and the motion trajectory. A prediction result of whether the subject and the radiation assembly are going to collide may be generated based on one or more distances between the moving radiation assembly and the subject (or referred to as the fourth distances).

In some embodiments, the fourth distances may be determined based on the fifth coordinates corresponding to the target area and the sixth coordinates corresponding to the motion trajectory of the radiation assembly. For example, using the equation (1). In some embodiments, at least one fourth distance may be determined. The at least one fourth distance may be a shortest distance between the subject and the motion trajectory of the radiation assembly. The determination module 420 may determine whether the fourth distance is less than a second threshold to predict whether the subject and the radiation assembly are going to collide. In some embodiments, the second threshold may be a value according to a default setting of the radiotherapy system 100, for example, 5 centimeters, 10 centimeters, 15 centimeters, 20 centimeters, etc., or may be adjustable according to different situations. In some embodiments, the second threshold may be specified by a user. If the at least one fourth distance is less than the second threshold, the prediction module 450 may generate the prediction result that the subject and the radiation assembly are going to collide.

In some embodiments, the processing device 140 may also generate alert information if the prediction result is that the subject and the radiation assembly are going to collide. The alert information may be transmitted to the terminal device 130 to alert the user (e.g., a doctor) of the RT system 100. The alert information may be in the form of text, an image, a video, an audio, a haptic alert, or the like, or a combination thereof. For example, the alert information may be displayed on a display of the terminal device 130. As another example, an alarm may go off on the terminal device 130 to alert the user.

In 705, the processing device 140 (e.g., the adjustment module 430) may adjust a position of the subject based on a prediction result of whether the subject and the radiation assembly are going to collide.

In some embodiments, if the prediction result is that the subject and the radiation assembly are going to collide, the adjustment module 430 may adjust the position of the subject. For instance, the adjustment module 430 may cause the table 115 to move away from the motion area of the radiation assembly. Alternatively, the user may manually adjust the position of the subject. If the subject is a patient, the user may inform the patient to change the position himself/herself. Similar descriptions regarding adjusting the position of the subject may be found elsewhere in the present disclosure. See, e.g., operations 505, 506, and 603, and relevant descriptions thereof.

It should be noted that the above description of the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 8:
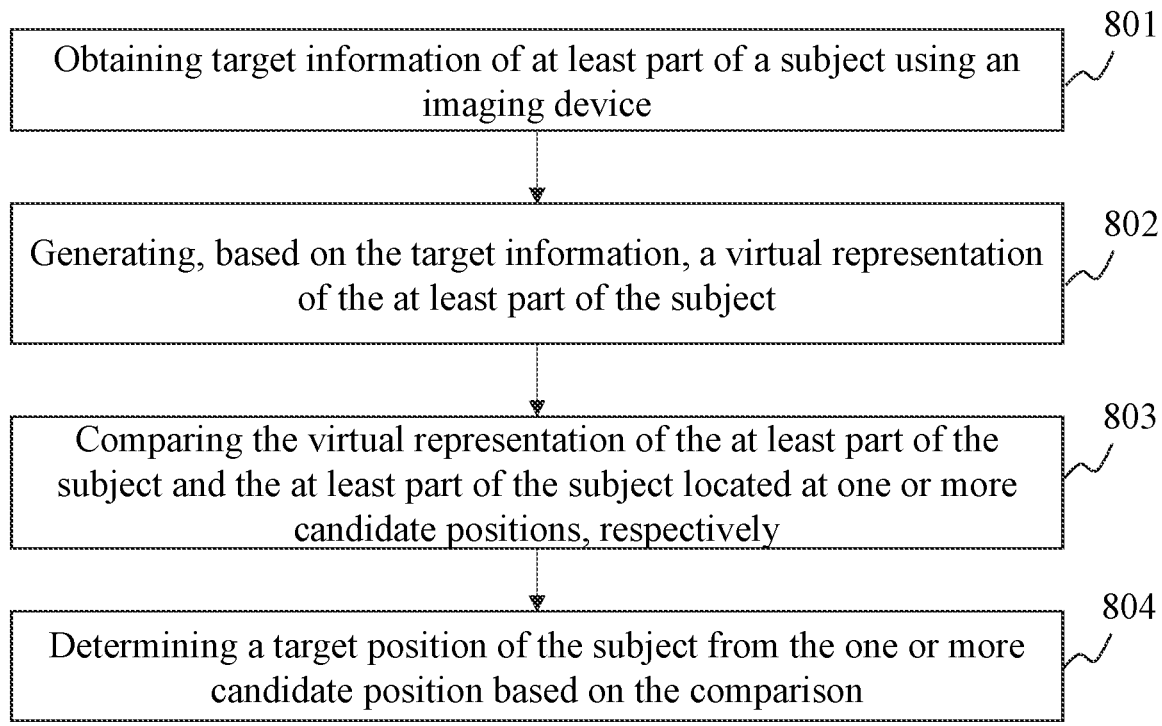
FIG. 8 is a flowchart illustrating an exemplary process for determining a target position of the subject according to some embodiments of the present disclosure.

FIG. 8 is a flowchart illustrating an exemplary process for determining a target position of the subject according to some embodiments of the present disclosure. In some embodiments, process 800 may be executed by the RT system 100. For example, the process 800 may be implemented as a set of instructions (e.g., an application) stored in a storage device (e.g., the storage device 150, the storage 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 800. In some embodiments, the process 800 may be another exemplary process for determining the target position of the subject different from the process 500.

In 801, the processing device 140 (e.g., the obtaining module 410) may obtain target information of at least part of a subject using an imaging device. In some embodiments, the obtaining module 410 may obtain third scanning data by causing the holographic projection device to image the at least part of the subject at a preset position using a millimeter wave. The preset position may be the same position described in operation 501. In some embodiments, the third scanning data and the target information may be similar to the first scanning data and the first information, respectively. The third scanning data may include at least raw projection data of the at least part of the subject, and information carried by reflected waves that are detected by the holographic projection device. Based on the third scanning data, the target information may include at least position information of the at least part of the subject, an image (e.g., a 3D image) of the at least part of the subject, or the like, or any combination thereof.

In 802, the processing device 140 (e.g., the prediction module 450) may generate a virtual representation of the at least part of the subject based on the target information.

In some embodiments, the virtual representation may be in the form of a hologram referring to an image that appears to be three dimensional and which can be seen with a naked eye (e.g., a virtual 3D image). The virtual representation may be of the same size as the at least part of the subject. In some embodiments, the virtual representation may be displayed at any position. For example, the virtual representation may be displayed on the table 115. As another example, the virtual representation may be displayed on a wall. In some embodiments, the virtual representation may be displayed in the preset position. The virtual representation may be generated directly by the holographic projection device.

In 803, the processing device 140 (e.g., the comparison module 460) may compare the virtual representation of the at least part of the subject and the at least part of the subject located at one or more candidate positions, respectively.

In some embodiments, the candidate position may be the same as the candidate position as described in 503, referring to a position at which the subject is located when being set up for radiation delivery. When the at least part of the subject is located at the candidate position, it may at least partially overlap with the virtual representation displayed at the preset position. The comparison module 460 may compare the virtual representation of the at least part of the subject and the at least part of the subject at the candidate position to determine an overlapping value. The overlapping value may indicate an overlapping degree of the virtual representation of the at least part of the subject and the at least part of the subject. The overlapping value may be presented in the form of a ratio, for example, 90%. For each of the one or more candidate positions, an overlapping value may be determined by the comparison module 460.

In 804, the processing device 140 (e.g., the determination module 420) may determine a target position of the subject from the one or more candidate positions based on the comparison. The target position may be the same as the target position as described in 506. After the one or more overlapping values are obtained, the determination module 420 may determine whether the overlapping value is greater than a third threshold, for example, 97%, 98%, or 99%. The candidate position corresponding to an overlapping value greater than the third threshold may be designated as the target position.

It should be noted that the above description of the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 9:
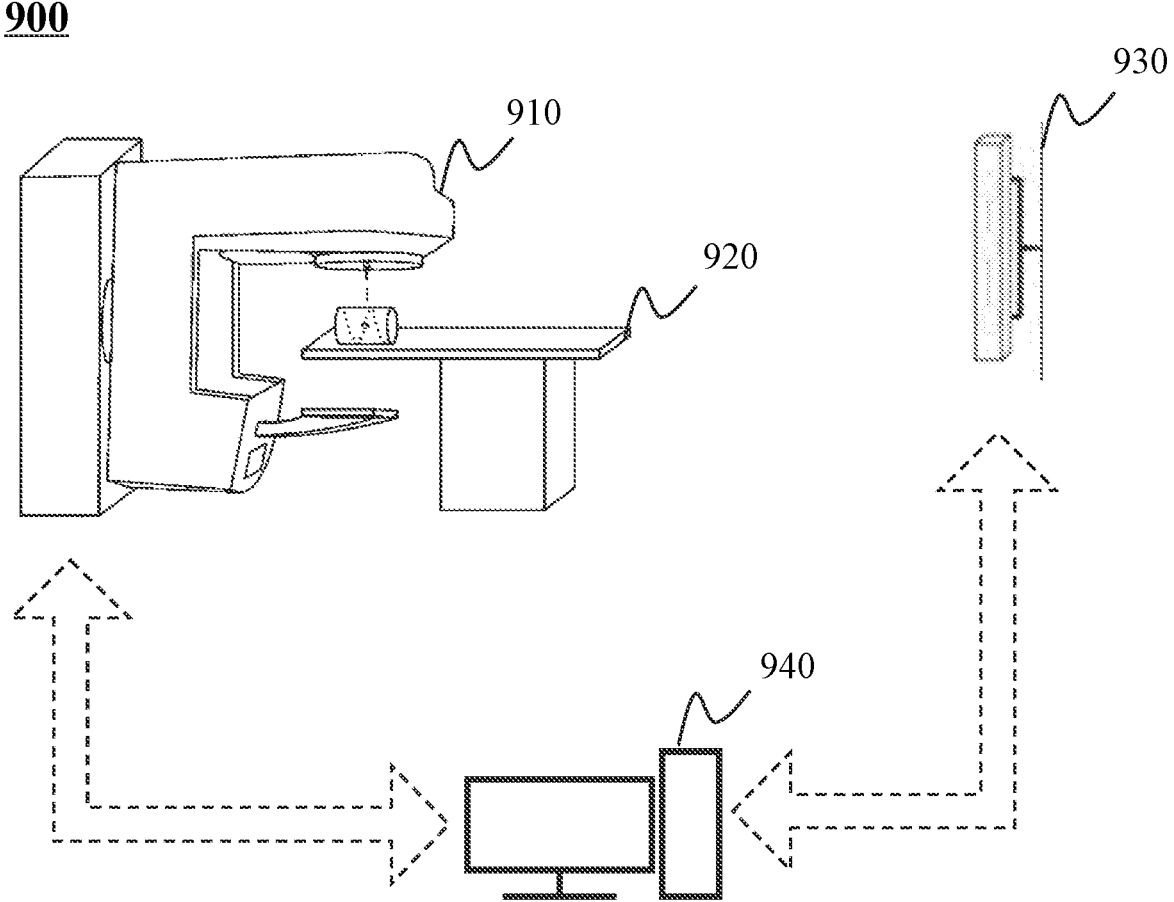
FIG. 9 is a schematic diagram illustrating an exemplary radiotherapy system according to some embodiments of the present disclosure.

FIG. 9 is a schematic diagram illustrating an exemplary radiotherapy system according to some embodiments of the present disclosure. As shown in FIG. 9, exemplary radiotherapy system 900 may include a radiation assembly 910, a table 920, a holographic projection device 930, and a processor 940.

The radiation assembly 910 may emit radiation beams. The radiation beam may be configured to irradiate a subject, for example, a patient, thereby killing cancer cells. The radiation beams may include α rays, β rays, γ rays, X-rays, electron rays, proton rays, or the like, or any combination thereof. The radiation assembly 910 may include a linear accelerator, a cyclotron, an electrostatic accelerator, a particle accelerator, a voltage doubling accelerator, or the like. The radiation assembly 910 may rotate, for example, around an axis of a gantry clockwise or counter clockwise to irradiate the subject from various directions within the range of 360 degrees. In some embodiments, the radiation assembly 910 may further include an electronic portal imaging device (EPID), which may collect radiation beams transmitted through the subject, for example, to image the subject.

The table 920 may support the subject (such as a patient). The subject may be placed on table 920 in a particular posture (for example, supine, prone, latericumbent, or the like) during radiotherapy treatment and/or radiotherapy localization. The table 920 may be a six-dimensional table. The table 920 may move along three directions of x, y, or z and rotate around three directions of x, y, or z, and thus may move at least part (such as, a region to be scanned, or a treatment region of a patient) of the subject to a position aligning with an isocenter of the radiation assembly 910 accurately and quickly. Thereby, during radiotherapy, it may be ensured that the radiation beams can be emitted to a treatment region of the subject (e.g., a patient) and the damages to and side effects on normal cells and/or tissue may be relatively small.

The holographic projection device 930 may scan a target area. In some embodiments, the target area may include at least part of the subject. The at least part of the subject may include an ROI of the subject (e.g., a region of a tumor, a region at risk including an organ or tissue at risk in the vicinity of the region of the tumor), a region at risk associated with the ROI (e.g., a region of an organ or tissue at risk in the vicinity of the tumor, a region in the vicinity of the organ or tissue at risk), or the like, or any combination thereof. In some embodiments, the target area may also include the whole subject. In some embodiments, the target area may include the subject and a motion area of a radiation assembly, for example, the radiation assembly 910. The holographic projection device 930 may scan the target area by emitting a millimeter wave to acquire scanning data. Based on the scanning data, position data of any point in the target area may be obtained. For example, the position data may include coordinates of any point of the target area, the coordinates may be defined by the camera coordinate system which is obtained by calibrating the holographic projection device 930 in advance. The holographic projection device 930 may also generate an image based on the scanning data, for example, a 3D image of the target area, and reproduce the target area based on the scanning data, for example, a 3D virtual representation.

The processor 940 may control the radiotherapy system 100, for example, control operations of one or more components of the radiotherapy system 900. Merely by way of illustration, the processor 940 may control the radiation assembly 910 to emit the radiation beams, control movement of the table 920, and control the scanning and image reproduction of the holographic projection device 930. The processor 940 may store executable instructions for execution. Upon executing the executable instructions, the processor 940 may control the components of the radiotherapy system 900. In some embodiments, the processor 940 may control the holographic projection device 930 to scan the subject, for example, during radiotherapy localization, and/or during treatment sessions of radiotherapy. After the scanning is completed, the processor 940 may obtain the target information. Referring to the description of the holographic projection device 930, the target information may include at least a target set of position data of the subject, and further a target image of the subject. In some embodiments, the processor 940 may also store the target information in its own storage device, or in an external storage device.

In some embodiments, the processor 940 may determine a target position of the subject based on the target information. For example, the target position may include a position at which the subject is scanned by the holographic projection device 930. In some embodiments, the position may be represented by the target set of position data of the subject (e.g., coordinates in the camera coordinate system). Alternatively or additionally, the position may be represented in the form of a 3D virtual representation. The 3D virtual representation may be displayed by controlling the holographic projection device 930 to perform a 3D image reproduction of the subject based on the scanning data of the subject. In some embodiments, the processor 940 may control the holographic projection device 930 to display the 3D virtual representation of the at least part of the subject. A displaying position of the 3D virtual representation may coincide with the position at which the subject is scanned by the holographic projection device 930.

In some embodiments, the target area may be scanned when the subject is located at a preset position. And the target information may be obtained based on the scanning data acquired by the holographic projection device 930 scanning the target area. The preset position may refer to a position of the subject when a region to be scanned (e.g., a region of a tumor) of the subject coincides with an isocenter of the radiation assembly 910. In some embodiments, the processor 940 may control the holographic projection device 930 to scan the target area when the subject located at a candidate position, and obtain candidate information of the subject. Similar to the target information, the candidate information may include at least a candidate set of position data of the subject. The candidate set of position data may include candidate coordinates of any point of the subject in the same coordinate system which defines the coordinates included in the target information. Based on the coordinates (e.g., the coordinates included in the candidate information and the target information) of each of one or more points of the subject, the processor 940 may generate a determination about the candidate position of the subject, for example, whether the subject located at the candidate position can receive the radiation. Merely by way of example, the processor 940 may determine whether a distance between two coordinates of a same point of the subject is less than a distance threshold, for example, 0.5 mm, 1 mm, 1.5 mm, 2 mm, etc. If the distance is less than the distance threshold, the processor 940 may determine that the subject located at the candidate position can receive the radiation, or vice versa.

In some embodiments, the processor 940 may control the holographic projection device 930 to generate a virtual representation of the at least part of the subject based on the target information. The virtual representation may be displayed in the preset position. And the processor 940 may compare the virtual representation of the subject and the subject located at one or more candidate positions, respectively. After comparison, the processor 940 may obtain one or more overlapping values indicating an overlapping degree of a virtual representation of the subject and the subject located at the candidate. The overlapping value may be represented by a ratio, for example, 90%. Based on the overlapping value, the processor 940 may determine a target position of the subject from the one or more candidate positions. For example, the candidate position corresponding to an overlapping value greater than a ratio threshold may be designated as the target position. In some embodiments, if there is no overlapping value greater than the ratio threshold, the processor 940 may control the table 920 to move to adjust the position of the subject, until an adjusted position corresponding to an overlapping value is greater than a ratio threshold. In some embodiments, the user (e.g., a doctor) of the radiotherapy system 900 may adjust the position of the subject (e.g., a patient) to the target position based on the virtual representation of the subject. For example, the user may control the table 920 to move to adjust the position of the subject by inputting moving control instructions. As another example, the user may manually move the position of the subject. As still another example, the user may direct the patient to move.

In some embodiments, the target area may include at least part of the subject, and a motion area of the radiation assembly 910. Since the radiation assembly 910 may be moved to more accurately irradiate the subject, in order to prevent the radiation assembly 910 from colliding with the subject, a relative position of the subject to the radiation assembly 910 may be detected in advance. The processor 940 may control the holographic projection device 930 to scan the target area to obtain scanning data, and obtain current information of the target area based on the obtained scanning data. The current information may include at least a current set of position data of the target area. In some embodiments, the current set of position data of the target area may be obtained by performing data processing on the obtained scanning data, such as coordinate transformation. Each of points of the target area may be assigned coordinates (or referred to as the current coordinates). The current coordinate may be defined by, for example, a 3D Cartesian coordinate system established with the isocenter of the radiation assembly 910 as the origin. Further, the processor 940 may obtain the motion trajectory of the radiation assembly 910 from a Therapy Planning System (TPS). The motion trajectory may include any position of the radiation assembly 910 at any time point during radiotherapy, and represented by a plurality of coordinates (or referred to as the motion coordinate). After that, the processor 940 may predict whether the subject and the radiation assembly 910 are going to collide based on the current information and the motion trajectory. For example, the processor 940 may first obtain one or more current distance based on the current coordinates and the motion coordinate. Then, the processor 940 may determine whether all the current distances are less than a threshold, e.g., 5 cm, 10 cm, 15 cm, 20 cm, etc. If the at least one current distance is less than the threshold, the processor 940 may generate a prediction result that the subject and the radiation assembly are going to collide. Furthermore, the processor 940 may issue an alarm, for example, buzzing. In some embodiments, the processor 940 may control the holographic projection device 930 to collect the scanning data of the radiation assembly 910 and the subject during the radiotherapy in real time, and the scanning data may be used to determine whether the radiation assembly 910 and the subject are going to collide.

In some embodiments, the processor 940 may control the holographic projection device 930 to scan the subject in real time and obtain information about the subject during radiation delivery, such as, treatment sessions of radiotherapy. The processor 940 may detect a change in the position of the subject based on the acquired information. For example, if an ROI of the subject deviates from the isocenter of the radiation assembly 910, the processor 940 may control the radiation assembly 910 to stop emitting the radiation beams to prevent exposure on normal cells. At the same time, the processor 940 may control the table 920 to automatically adjust the position of the subject, or remind the user (e.g., a doctor) to manually adjust the position of the subject. When the subject is moved to the correct position, the processor 940 may control the radiation assembly 910 to continue to re-radiate the subject. In some embodiments, a treatment region may be affected by physiological movement, and the position thereof may change periodically. For example, a periodic undulating motion occurs in the chest and abdomen of a patient due to respiratory motion. To accurately radiate the treatment region, the processor 940 may control the time to emit radiation beams based on the acquired information. For example, images of the chest and abdomen surface caused by the respiratory motion of the patient may be collected in advance, and the time to emit the radiation beams may be set based on the images. During the treatment, a virtual 3D image of the subject may be obtained using the millimeter wave in real time, and compared with the images to determine whether the beam is released, thereby more accurately delivering the treatment beams to the target region, reducing damages to surrounding crisis organs or tissue, and improving treatment accuracy.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim.

Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for positioning a subject, implemented on a computing device having one or more processors and one or more storage devices, the method comprising:
    obtaining a first three-dimensional (3D) surface image of at least part of a subject when the subject is located at a preset position;
    generating a virtual representation of the at least part of the subject based on the first 3D surface image;
    displaying the virtual representation of the at least part of the subject at the preset position and superimposing the virtual representation on the subject to mimic the at least part of the subject that is inside the subject;
    obtaining a second 3D surface image of the at least part of the subject when the subject is located at a candidate position; and
    determining, based on the displayed virtual representation of the at least part of the subject or the first 3D surface image and the second 3D surface image, whether the candidate position of the subject meets the requirement of a target position of the subject.

2. The method of claim 1, wherein the determining, based on the displayed virtual representation of the at least part of the subject or the first 3D surface image and the second 3D surface image, whether the candidate position of the subject meets the requirement of a target position of the subject, includes:
    determining, based on the first 3D surface image, a first position of each of one or more feature points located on the at least part of the subject;
    determining, based on the second 3D surface image, a second position of each of the one or more feature points;
    for each feature point of the one or more feature points, determining a first distance between the first position and the second position; and
    determining, based at least in part on the one or more first distances, whether the candidate position of the subject meets the requirement of the target position of the subject.

3. The method of claim 2, wherein the one or more feature points include at least a marker located on a surface of the subject, the marker indicating a region of interest (ROI) of the subject.

4. The method of claim 2, wherein the determining, based at least in part on the one or more first distances, whether the candidate position of the subject meets the requirement of the target position of the subject includes:
    determining whether the one or more first distances are less than a first threshold.

5. The method of claim 4, further includes:
    determining a target position of the subject based on a determination result of whether the one or more first distances are less than the first threshold.

6. The method of claim 5, wherein the determination result includes that at least one of the one or more first distances is less than the first threshold, and the determining the target position of the subject includes:
    designating the candidate position as the target position of the subject.

7. The method of claim 5, wherein the determination result includes that at least one of the one or more first distances exceeds the first threshold, and the determining the target position of the subject includes:
    adjusting the candidate position of the subject to an adjusted position such that, for each of the one or more feature points, a second distance between a third position of the feature point and the first position of the feature point is less than the first threshold, wherein the third position is obtained based on third information of the at least part of the subject, and the third information includes at least a third set of position data of the at least part of the subject; and
    designating the adjusted position as the target position of the subject.

8. The method of claim 2, further comprising:
    obtaining fourth information of the at least part of the subject using the imaging device at a time interval during a radiation session, the fourth information including at least a fourth set of position data of the at least part of the subject;
    determining, based on the fourth information, a fourth position of each of the one or more feature points; and
    causing, based on a third distance between the fourth position and the first position of each of the one or more feature points, a radiation assembly to perform a preset operation corresponding to the third distance.

9. The method of claim 8, wherein the causing, based on a third distance between the fourth position and the first position of each of the one or more feature points, a radiation assembly to perform a preset operation corresponding to the third distance includes:
controlling an operation of the radiation assembly based on a second determination result of whether the third distance is less than the first threshold.

10. The method of claim 9, wherein the second determination result includes that the third distance exceeds the first threshold, and the controlling an operation of the radiation assembly based on a second determination result of whether the third distance is less than the first threshold includes:
causing the radiation assembly to stop emitting radiation beams.

11. The method of claim 1, wherein the obtaining a second 3D surface image of the at least part of the subject when the subject is located at a candidate position includes:
obtaining, using an imaging device, the second 3D surface image of the at least part of the subject when the subject is located at the candidate position.

12. The method of claim 11, wherein the imaging device includes a holographic projection device, and the obtaining the second 3D surface image of the at least part of the subject includes:
obtaining first scanning data by causing the holographic projection device to image the subject using a millimeter wave; and
obtaining the second 3D surface image based on the first scanning data.

13. The method of claim 1, further comprising:
obtaining second scanning data by scanning a target area, wherein the target area includes the subject and a motion area of a radiation assembly;
obtaining fifth information of the target area based on the second scanning data, the fifth information including at least a fifth set of position data of the target area;
obtaining a motion trajectory of the radiation assembly;
predicting, based on the fifth information and the motion trajectory, whether the subject and the radiation assembly are going to collide; and
adjusting a position of the subject based on a prediction result of whether the subject and the radiation assembly are going to collide.

14. The method of claim 13, wherein the predicting, based on the fifth information and the motion trajectory, whether the subject and the radiation assembly are going to collide includes:
determining, based on coordinates corresponding to the target area and coordinates corresponding to the motion trajectory of the radiation assembly, at least one distance; and
generating, based on a determination result that the at least one distance is less than a threshold, a prediction result that the subject and the radiation assembly are going to collide.

15. The method of claim 1, wherein t the determining, based on the displayed virtual representation of the at least part of the subject or the first 3D surface image and the second 3D surface image, whether the candidate position of the subject satisfies a condition for radiation delivery, includes:
determining the target position of the subject from one or more candidate positions based on an overlapping degree of the virtual representation of the at least part of the subject and the at least part of the subject.

16. A system for positioning a subject, comprising:
at least one storage device including a set of instructions or programs; and
at least one processor configured to communicate with the at least one storage device, wherein when executing the set of instructions or programs, the at least one processor is configured to cause the system to perform operations including:
obtaining a first three-dimensional (3D) surface image of at least part of a subject when the subject is located at a preset position;
generating a virtual representation of the at least part of the subject based on the first 3D surface image;
displaying the virtual representation of the at least part of the subject at the preset position and superimposing the virtual representation on the subject to mimic the at least part of the subject that is inside the subject;
obtaining a second 3D surface image of the at least part of the subject when the subject is located at a candidate position; and
determining, based on the displayed virtual representation of the at least part of the subject or the first 3D surface image and the second 3D surface image, whether the candidate position of the subject meets the requirement of a target position of the subject.

17. The system of claim 16, wherein to determine, based on the displayed virtual representation of the at least part of the subject or the first 3D surface image and the second 3D surface image, whether the candidate position of the subject meets the requirement of a target position of the subject, the at least one processor is further configured to cause the system to perform the operations including:
determining, based on the first 3D surface image, a first position of each of one or more feature points located on the at least part of the subject;
determining, based on the second 3D surface image, a second position of each of the one or more feature points;
for each feature point of the one or more feature points, determining a first distance between the first position and the second position; and
determining, based at least in part on the one or more first distances, whether the candidate position of the subject meets the requirement of the target position of the subject.

18. The system of claim 17, wherein the one or more feature points include at least a marker located on a surface of the subject, the marker indicating a region of interest (ROI) of the subject.

19. The system of claim 16, wherein the determining, based on the displayed virtual representation of the at least part of the subject or the first 3D surface image and the second 3D surface image, whether the candidate position of the subject satisfies a condition for radiation delivery includes:
determining the target position of the subject from one or more candidate positions based on an overlapping degree of the virtual representation of the at least part of the subject and the at least part of the subject.

20. A non-transitory computer readable medium storing instructions, the instructions, when executed by at least one processor, causing the at least one processor to implement a method comprising:
obtaining a first three-dimensional (3D) surface image of at least part of a subject when the subject is located at a preset position;

generating a virtual representation of the at least part of the subject based on the first 3D surface image;

displaying the virtual representation of the at least part of the subject at the preset position and superimposing the virtual representation on the subject to mimic the at least part of the subject that is inside the subject;

obtaining a second 3D surface image of the at least part of the subject when the subject is located at a candidate position; and determining, based on the displayed virtual representation of the at least part of the subject or the first 3D surface image and the second 3D surface image, whether the candidate position of the subject meets the requirement of a target position of the subject.

* * * * *